United States Patent
Shtein et al.

(10) Patent No.: US 12,240,852 B2
(45) Date of Patent: Mar. 4, 2025

(54) CO-CRYSTALS, METHOD AND APPARATUS FOR FORMING THE SAME

(71) Applicant: THE REGENTS OF THE UNIVERSITY OF MICHIGAN, Ann Arbor, MI (US)

(72) Inventors: Max Shtein, Ann Arbor, MI (US); Siddharth Borsadia, Ann Arbor, MI (US); Eugene Shteyn, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 937 days.

(21) Appl. No.: 17/312,966

(22) PCT Filed: Dec. 11, 2019

(86) PCT No.: PCT/US2019/065679
§ 371 (c)(1),
(2) Date: Jun. 11, 2021

(87) PCT Pub. No.: WO2020/123625
PCT Pub. Date: Jun. 18, 2020

(65) Prior Publication Data
US 2022/0048911 A1 Feb. 17, 2022

Related U.S. Application Data

(60) Provisional application No. 62/778,072, filed on Dec. 11, 2018.

(51) Int. Cl.
*C07D 473/12* (2006.01)
*A61L 31/08* (2006.01)
*C07C 51/43* (2006.01)

(52) U.S. Cl.
CPC ............ *C07D 473/12* (2013.01); *A61L 31/08* (2013.01); *C07C 51/43* (2013.01); *C07B 2200/13* (2013.01)

(58) Field of Classification Search
CPC ... C07D 473/12; C07C 51/43; C07B 2200/13; A61L 31/08
See application file for complete search history.

(56) References Cited

U.S. PATENT DOCUMENTS

| | | |
|---|---|---|
| 7,026,187 B2 | 4/2006 | Shtein et al. |
| 7,404,862 B2 | 7/2008 | Shtein et al. |
| 7,431,968 B1 | 10/2008 | Shtein et al. |
| 7,722,927 B2 | 5/2010 | Shtein et al. |
| 7,744,957 B2 | 6/2010 | Forrest et al. |
| 7,897,210 B2 | 3/2011 | Shtein et al. |
| 8,535,759 B2 | 9/2013 | Forrest et al. |

FOREIGN PATENT DOCUMENTS

| | | |
|---|---|---|
| WO | WO-2007/053536 A2 | 5/2007 |
| WO | WO-2010/013035 A1 | 2/2010 |
| WO | WO-2017/009813 A1 | 1/2017 |

OTHER PUBLICATIONS

Zhang, J Crystal Growth, 469, 2017, 114-118. (Year: 2017).*
Korotkova, Procedia Chemistry, 10, 2014, 473-476. (Year: 2014).*
Friscic, 2007, Crystal Growth and Design, 2008, vol. 8(5), 1605-1609. (Year: 2008).*
Jadhav, J pharm Sci Tech Mgmt, vol. 2(1), 2016, 7-16. (Year: 2016).*
Berge et al., Pharmaceutical Salts, J. Pharm. Sci., 66:1-19 (1977).
Bolton et al., Improved stability and smart-material functionality realized in an energetic cocrystal, Angew. Chem. Int. Ed. Engl., 50(38):8960-3 (2011).
Childs et al., Crystal engineering approach to forming cocrystals of amine hydrochlorides with organic acids. Molecular complexes of fluoxetine hydrochloride with benzoic, succinic, and fumaric acids, J. Am. Chem. Soc., 126(41):13335-42 (2004).
Friscic et al., Recent Advances in Understanding the Mechanism of Cocrystal Formation via Grinding, Cryst. Growth Des., 9(3):1621-37 (2009).
Gill et al., Coated microneedles for transdermal delivery, J. Control. Release, 117(2):227-37 (2007).
Good et al., Solubility Advantage of Pharmaceutical Cocrystals. Crystal Growth & Design, 9(5), 2252-2264 (2009).
Gray, Alteration of leaf size and shape and other changes caused by gibberellins in plants, Am. J. Botany, 44(8):674-82 (1957).
International Application No. PCT/US19/65679, International Search Report and Written Opinion, mailed Apr. 9, 2020.
Ji et al., Identification of an antibacterial compound, benzylideneacetone, from Xenorhabdus nematophila against major plant-pathogenic bacteria, FEMS Microbiol. Lett., 239(2):241-8 (2004).
Karimi-Jefari et al., Creating Cocrystals: A Review of Pharmaceutical Cocrystal Preparation Routes and Applications, Cryst. Growth Des., 18(10):6370-87 (2018).
Kuminek et al., Cocrystals to facilitate delivery of poorly soluble compounds beyond rule of 5, Adv. Drug Deliv. Rev., 101:143-66 (2016).
Lara-Ochoa et al., Cocrystals definitions, Supramolecular Chemistry, 19(8):553-7 (2007).
Miyake et al., Toxicities of and inflammatory responses to moxifloxacin, cefuroxime, and vancomycin on retinal vascular cells, Sci. Rep., 9(1):9745 (2019).
Musumeci et al., Virtual cocrystal screening, Chemical Science, 2(5), 883 (2011).

(Continued)

*Primary Examiner* — D Margaret M Seaman
(74) *Attorney, Agent, or Firm* — MARSHALL, GERSTEIN & BORUN LLP

(57) ABSTRACT

Disclosed herein is a method and apparatus for synthesizing co-crystals from the vapor phase without the need for liquid solvent. Also disclosed herein are co-crystals formed from the vapor phase, substrates coated with said co-crystals, pharmaceutical compositions thereof and apparatuses for producing said co-crystals.

20 Claims, 11 Drawing Sheets

(56) References Cited

OTHER PUBLICATIONS

Nartowski et al., Tuning the spontaneous formation kinetics of caffeine: malonic acid co-crystals, CrystlEngComm., 18:2617-20 (2016).

Qiao et al., Pharmaceutical cocrystals: an overview, Int. J. Pharm., 419(1-2):1-11 (2011).

Rodríiguez-Hornedo et al., Reaction Crystallization of Pharmaceutical Molecular Complexes, Mol. Pharm., 3(3):362-367 (2006).

Sathisaran et al., Engineering cocrystals of poorly water-soluble drugs to enhance dissolution in aqueous medium, Pharmaceutics, 10(3):108 (2018).

Schultheiss et al., Nutraceutical cocrystals: utilizing pterostilbene as a cocrystal former, CrystEngComm., 2010,12, 2436-2442.

Shalev et al., Printing of small molecular medicines from the vapor phase, Nat. Commun., 8(1):711 (2017).

Shan et al., The role of cocrystals in pharmaceutical science, Drug Discov. Today, 13(9-10):440-6 (2008).

Subrahmanyam et al., Bioequivalence studies of two formulations of famciclovir tablets by HPLC method, Asian Journal of Chemistry, 2007, vol. 19, No. 6 (2007), 4245-4250.

Taylor et al., Evaluating the energetic driving force for cocrystal formation, Cryst. Growth Des., 18:892-904 (2018).

Trask et al., Pharmaceutical cocrystallization: engineering a remedy for caffeine hydration, Crystal Growth & Design, 5(3):1013-21 (2005).

Vishweshwar et al., Pharmaceutical co-crystals, J. Pharm. Sci., 95(3):499-516 (2006).

Wang et al., Sweet Theophylline Cocrystal with Two Tautomers of Acesulfame, Cryst. Growth Des., 15(6):2574-8 (2015).

Selvaraj et al., Growth of phthalocyanine doped anthracene crystal using a three-zone furnace by vacuum sublimation method, J. Crystal Growth, 225(2-4):168-72 (May 2001).

Thompson et al., Thin films of a ferroelectric phenazine/chloranilic acid organic cocrystal, J. Crystal Growth, 327(1):258-61 (May 2011).

Zhang et al., Preparation of 2:1 urea-succinic acid cocrystals by sublimation, J. Crystal Growth, 469:114-8 (Sep. 2016).

Eddleston et al., Screening for polymorphs of cocrystals: a case study, Crystengcomm, 15(1):175-81 (Jan. 2013).

Wu et al., Simultaneous DSC-FTIR microspectroscopy used to screen and detect the co-crystal formation in real time, Bioorg. Med. Chem. Lett., 21(10):3148-51 (Mar. 2011).

European Patent Application No. 19896768.9, Partial Supplementary European Search Report, dated Aug. 5, 2022.

* cited by examiner

FIG. 5
Morphology Comparison (1000x Magnification)
| Caffeine | Succinic Acid | Co-crystal |
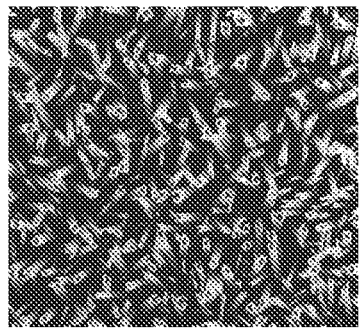 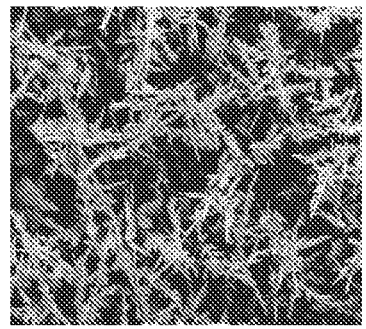 
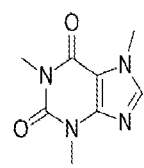 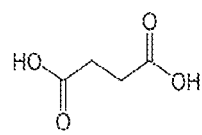 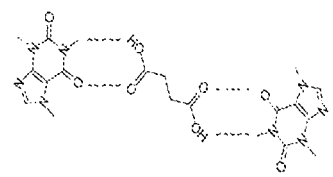

CO-CRYSTALS, METHOD AND APPARATUS FOR FORMING THE SAME

STATEMENT OF US GOVERNMENT SUPPORT

This invention was made with government support under grant numbers 4500002489, 4500002490, 1827123, and 1240264, awarded by the National Science Foundation. The government has certain rights in the invention.

BACKGROUND

Technical Field

The present disclosure relates to methods and apparatuses for synthesizing co-crystals from the vapor phase without the need for liquid solvent, and co-crystals formed using the methods described. The disclosure further relates to methods of coating substrates, such as medical devices, with co-crystals, as well as co-crystal-coated substrates.

Description of Related Technology

Co-crystals have applications, among others, in improving the administration of low solubility drugs (e.g. carbamazepine, used in the treatment of epilepsy and neuropathic pain). Pharmaceutical co-crystals are supramolecular systems that allow for enhanced release and/or concentration of an active pharmaceutical ingredient ("API") in vivo, without modifying its molecular structure. Co-crystals of APIs often show a solubility advantage ("SA") when compared to the pure API because a higher dynamic concentration of the API can be attained in a biological system. See Childs et al., Journal of the American Chemical Society, 126, 13335, (2004). This SA can be useful for enhancing the concentration, and therefore effectiveness, of poorly water-soluble molecules. Furthermore, different co-crystal formers ("coformers"), or even different processing conditions/methods, can yield co-crystals of the same API with different SAs, to meet the needs of different applications.

In most pharmaceutical applications, it is desirable that the co-crystal be stable at or around room temperature before being exposed to the liquid environment. Conventionally, a co-crystal comprises one or more coformer(s) and, in pharmaceutical applications, an API. They are distinguished from other solid forms incorporating APIs in that the coformer is non-charged, and thus, does not involve any proton transfer, as is the case with salts. Additionally, conventional co-crystals incorporate a coformer that itself is a solid at the temperature of interest, in contrast to solids that have a liquid component, such as solvates or hydrates. The packing and crystal structure of the co-crystal differ from those of the pure ingredients, typically distinguished by a different x-ray diffraction ("XRD") pattern, while the chemical composition of the individual organic compounds remains unchanged.

In conventional solid dosage forms, APIs are often mixed with a variety of additives, known as excipients. These additional components are used to give the final drug product more desirable physical and chemical properties, such as enhanced disintegration times and yield strength of the solid dosage form (e.g., a tablet). A key distinction between excipients and coformers, understood by those skilled in the art, is that excipients do not change the crystal structure of the API in the solid dosage form, such as a tablet. A coformer does alter the phase of the drug itself and thus changes its dissolution behavior even if no excipient is present.

There are significant problems with current methods of creating co-crystals, such as pharmaceutical co-crystals, which limit their use to a particular form (e.g., a bulk powder) using a limited set of compounds, delivery methods, compositions, and concentrations. Traditional methods for forming co-crystals involve the use of either high energy grinding or precipitation from an evaporating solution, involving a liquid solvent and a number of steps and conditions, prior to the numerous steps and processes used to create the final dosage form. These requirements pose significant disadvantages for material compatibility, access to different compositions of matter, process control, product quality, ability to incorporate co-crystals into different dosage forms for pharmaceutical applications, and high manufacturing costs. See Vishweshwar et al., Journal of Pharmaceutical Sciences, 95(3):499-516 (2006).

Therefore, there is a need for new methods and apparatuses for producing co-crystals, particularly of pharmaceutical compounds, and new methods of tuning the properties of co-crystals for different applications.

SUMMARY

Provided herein are methods of forming a co-crystal of an organic compound and a coformer comprising: (a) subliming and/or evaporating the organic compound optionally in the presence of an organic compound carrier gas to form a organic compound vapor; (b) subliming and/or evaporating the coformer optionally in the presence of a coformer carrier gas to form a coformer vapor; (c) mixing the organic compound vapor and the coformer vapor, optionally in the presence of a mixing gas, to form a vapor mixture, wherein the vapor mixture comprises a molar ratio of the organic compound and the coformer of 10:1 to 1:10; and (d) condensing the vapor mixture onto a substrate to form the co-crystal; wherein: the co-crystal comprises the organic compound and the coformer hydrogen bonded together, optionally in a ratio of 1:3 to 3:1; the organic compound is sublimed at a temperature that is 10° C. to 100° C. above its onset of sublimation, as determined by thermogravimetric analysis ("TGA"); the substrate is at a temperature of −50° C. to 50° C.; and the co-crystal is stable at 25° C., characterized by differential scanning calorimetry, microscopy, X-ray diffraction, or a combination thereof.

In some embodiments, the substrate is coated with the co-crystal during step (d). In some cases, the substrate comprises quartz, glass, metal, plastic, ceramic, or combinations thereof. In various cases, the substrate is temperature-controlled. In various cases, the molar ratio of organic compound to coformer in the vapor mixture is 1:3 to 1:5. In various embodiments, the molar ratio of organic compound to coformer in the vapor mixture is 1:1.1 to 1:1.5. In some embodiments, the molar ratio of organic compound to coformer in the vapor mixture is 1:1.

In some cases, the co-crystal comprises the organic compound and coformer in a molar ratio of 2:1 to 1:2. In some embodiments, the co-crystal comprises the organic compound and coformer in a molar ratio of 1:1.5 to 1.5:1. In some cases, the co-crystal comprises the organic compound and coformer in a molar ratio of 1:1.

In various embodiments, the organic compound has a vapor pressure of $10^{-3}$ Pascals to $10^6$ Pascals. In some embodiments, the organic compound has a molar mass of 100-1000 g/mol. In various cases, the organic compound is an active pharmaceutical ingredient ("API"). In various cases, the organic compound is selected from the group consisting of caffeine, carbamazepine, 5-methoxy sulfadiazine, ethenzamide, nalidixic acid, isoniazid, furosemide, sulfadimidine, celecoxib, temozolamide, piroxicam, tryptamine, chlorzoxazone, p-coumaric, itraconazole, fluoxetine, telaprevir, sildenafil, theophylline, aceclofenac, 5-nitrouracil, indomethacin, aripiprazole, and atorvastatin, or a mixture thereof.

In some embodiments, the coformer comprises one or more hydrogen bonding functional groups. In various embodiments, the coformer comprises a carboxylic acid, alcohol, ketone, aldehyde, amide, amine, heterocycle comprising at least one N or O ring atom, or combinations thereof. In some cases, the coformer is selected from the group consisting of benzoic acid, oxalic acid, malonic acid, succinic acid, maleic acid, fumaric acid, glutaric acid, adipic acid, pimelic acid, 3,5-dihydroxybenzoic acid, triflouroacetic acid, 2,5-dihydroxybenzoic acid, 2,4-dihydroxybenzoic acid, m-nitrobenzoic acid, 5-chlorosalicylic acid, saccharin, citric acid, tartaric acid, 2,3-dihydroxybenzoic acid, 3,4-dihydroxybenzoic acid, barbital, 4-hydroxybenzoic acid, 1-hydroxy-2-naphthoic acid, malic acid, 3-hydroxybenzoic acid, 6-hydroxy-2-naphthoic acid, methylgallate, salicyclic acid, 2-hydroxybenzoic acid, formic acid, 3-hydroxy-2-naphthoic acid, sulfacetamide, acetic acid, sulfaproxyline, sulfuric acid, sulfamic acid, ethylenediamine, octadecylamine, glucono-delta lactone, allocitric acid, sucralose, indole, 1-hydroxyethyldene-1,1-diphosphonic acid, skatole, 5-chlorosalicylic acid, urea, 5-nitroisophthalic acid, trimesic acid, gentisic acid, ketoglutaric acid, adamantine tricarboyxlic acid, t-butylhydroquinone, isocirtric acid, trifluoroethanol, camphoric acid, 4-aminobenzoic acid, 2,6-pyridinedicarboxylic acid, aspirin, butyric acid, formamide, nicotinamide, nitromethane, 1,4-benzoquinone, glycolic acid, terephtalaldehyde, dioxane, N-methylpyrrolidone, dimethylsulfoxide, dimethylacetamide, acetone, dimethylformamide, furfural, and 4,4'-bipyridine, or a mixture thereof.

In various embodiments, step (a) is performed in the presence of the organic compound carrier gas. In some embodiments, the organic compound carrier gas carries the organic compound to a mixing chamber prior to step (c). In some cases, the organic compound carrier gas has a flow rate of about 1 to 150 standard cubic centimeters per minute ("sccm"). In some cases, the organic carrier gas flow rate is about 25 to 50 sccm. In some embodiments, the organic compound carrier gas comprises nitrogen, carbon dioxide, argon, hydrogen, helium, oxygen, water, methane, nitrous oxide or a mixture thereof. In various cases, step (b) is performed in the presence of the coformer carrier gas. In some embodiments, the coformer carrier gas carries the coformer to a mixing chamber prior to step (c). In some cases, the coformer carrier gas has a flow rate of about 1 to 150 sccm. In some cases, the coformer carrier gas flow rate is about 25 to 50 sccm. In some cases, the coformer carrier gas comprises nitrogen, carbon dioxide, argon, hydrogen, helium, oxygen, water, methane, nitrous oxide or a mixture thereof. In some embodiments, step (c) is performed in the presence of the mixing gas. In various embodiments, the mixing gas carries the vapor mixture to the substrate. In some cases, the mixing gas has a flow rate of about 1 to 150 sccm. In some cases, the mixing gas flow rate is 10 to 50 sccm. In some embodiments, the mixing gas comprises nitrogen, carbon dioxide, argon, hydrogen, helium, oxygen, water, methane, nitrous oxide or a mixture thereof. In some cases, the mixing gas comprises nitrogen. In some embodiments, the mixing gas is exposed to a guard flow gas prior to step (d), such that the guard flow gas surrounds the mixing gas, and the mixing gas comprises the vapor mixture. In various cases, the guard flow gas comprises nitrogen, carbon dioxide, argon, hydrogen, helium, methane, nitrous oxide or a mixture thereof.

In some embodiments, the substrate has a temperature of 5° C. to 25° C. In various cases, the substrate has a temperature of 15° C. In some cases, the substrate is a medical device. In some embodiments, the medical device is selected from the group consisting of a stent, needle, microneedle, syringe, cannula, catheter, sponge, clip, mesh, bandage, gauze, dressing, tape, swab, burn dressing, staple, implant, contact lens, medical tubing, adhesive patches, endoscopic device, punctal plugs, buccal patches, lingual patches, sub-lingual patches, electrode patches, and combinations thereof. In some cases, the medical device is a stent, needle, or sponge. In some embodiments, the vapor mixture is moved over the substrate during step (d). In some cases, the substrate is moved under the vapor mixture during step (d).

Also provided are substrates coated with a co-crystal produced by methods described herein. Further provided are co-crystals produced by the methods described herein. In embodiments, the co-crystals produced by the methods described herein include caffeine and succinic acid. In embodiments, the co-crystals produced by the methods described herein include indomethacin and saccharine.

The disclosure also provides co-crystals comprising caffeine and succinic acid, characterized by an X-ray diffraction pattern ("XRD") pattern comprising peaks at 14, 18, and 22±0.2° 2θ using Cu Kα radiation. In some embodiments, the co-crystal has a differential scanning calorimery ("DSC") thermogram substantially as shown in FIG. 4. In some embodiments, the caffeine and succinic acid are present in the co-crystal at a molar ratio of about 1:1.

Also provided herein are pharmaceutical compositions comprising the above mentioned co-crystals and a pharmaceutically acceptable carrier.

Further provided are apparatuses for producing a co-crystal as disclosed herein. In various cases, the apparatus comprises a housing having (i) a vapor mixing chamber adjacent to a jet exiting nozzle end of the housing; and (ii) a receiving end opposite the jet exiting nozzle end; the vapor mixing chamber being adjacent to a temperature control shroud for controlling the temperature of a vapor mixture of the organic compound and the coformer in the vapor mixing chamber; a first tubular internal container for injecting an organic compound and positioned within the receiving end, having (i) an outlet nozzle for feeding the organic compound into the vapor mixing chamber; (ii) a organic compound carrier gas inlet tube; and (iii) a thermocouple at a proximal end for controlling evaporation temperature of the first tubular internal container; and a second tubular internal container for injecting the coformer and positioned within the receiving end, having (i) an outlet nozzle for feeding the coformer into the vapor mixing chamber, (ii) a coformer carrier gas inlet tube, and (iii) a thermocouple at a proximal end for controlling evaporation temperature of the second tubular internal container, wherein at least one of the first tubular container and the second tubular container has a mixing gas inlet. In various cases, the apparatus further comprises a substrate for depositing the co-crystal. In some cases, the apparatus further comprises a temperature controller for controlling the temperature of the substrate.

Further aspects and advantages will be apparent to those of ordinary skill in the art from a review of the following detailed description, taken in conjunction with the drawings. The description hereafter includes specific embodiments with the understanding that the disclosure is illustrative, and is not intended to be limited to the specific embodiments described herein.

BRIEF DESCRIPTION OF THE DRAWINGS

FIG. 5 depicts morphological comparison between deposited films of caffeine, succinic acid, and a co-crystal of caffeine and succinic acid. All three films were deposited under the same conditions (source temperature, substrate temperature, flow rates, separation distance, and raster conditions).

DETAILED DESCRIPTION

Figure 1:
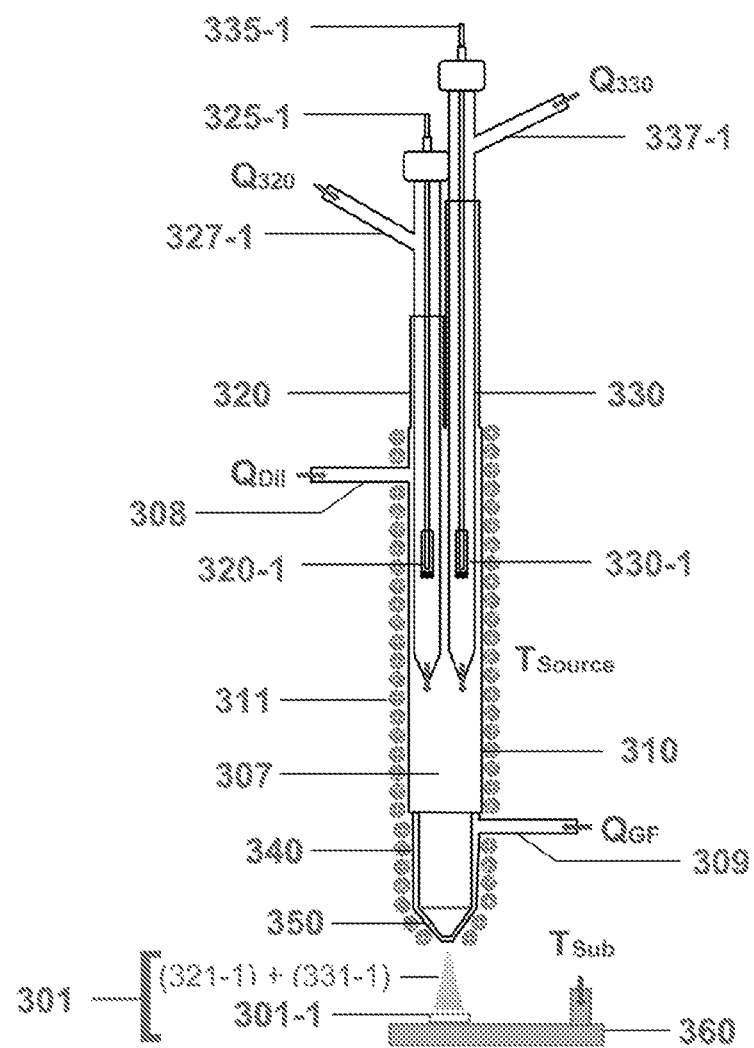
FIG. 1 depicts an embodiment of a dual nozzle organic vapor co-crystallization ("OVCC") apparatus disclosed herein.

Described herein are methods and apparatuses for forming stable co-crystals that use novel vapor deposition techniques, which allow the production of stable co-crystals that were previously unattainable (e.g., co-crystals of caffeine and succinic acid), and also enable the deposition of complex co-crystals (e.g., co-crystals containing active ingredients, passive ingredients, and diagnostic ingredients) on substrates, such as medical devices (e.g., implants, stents, contact lenses, capillaries, needles, and surgical instruments), internal and external surfaces, active electronic devices, test probes, and a variety of 3-dimensional objects, which also could not be achieved prior to the discovery described herein. The co-crystals may also be deposited on activatable medicant delivery devices and surfaces. The methods herein are designed to deposit co-crystals on a variety of 3-D objects and further, can be used in combination with methods of organic vapor jet deposition described in U.S. Pat. Nos. 7,897,210 B2, 7,722,927 B2, 7,431,968 B1, or 7,404,862 B2, or other deposition methods, such as those described in U.S. Pat. Nos. 7,744,957 B2, 8,535,759 B2, or 7,026,187 B2, each of which is incorporated herein by reference. Thus, also provided herein are methods and apparatuses for coating of substrates, such as medical devices, with co-crystals. As used herein, the term "coating" refers to a layer or covering on a substrate having a thickness from about 5 nm to 10 micrometers. The coating can be discontinuous or continuous and rough or smooth. The methods and apparatuses herein can be used to form a co-crystal coating on a substrate. In some embodiments, the coating can be a film. As used herein, the term "film" refers to a smooth, continous coating. The coating, such as a film, can grow on the substrate by any mode known in the art. In embodiments, the coating can have a "layer-plus island" morphology. A "layer-plus island" morphology refers to a morphology in which three-dimensional islands of the co-crystals described herein are layered on top of a two-dimensional deposited layer which may or may not be a co-crystal, as described herein, as well. In embodiments, the two-dimensional deposited layer upon which the island is layered is a co-crystal as described herein. In embodiments, the two-dimensional deposited layer upon which the island is layered is not a co-crystal as described herein. In embodiments, the coating can have an "island" morphology. An "island" morphology refers to a morphology in which three-dimensional islands of co-crystals are layered directly on top of the substrate. In embodiments, the co-crystals exhibit solid or hollow needle-like morphology, solid or hollow long wires having thickness ranging from several nanometers (e.g., from about 10 nanometers) to several micrometers (e.g., up to 10 micrometers), whiskers, branched structures, spheroidal particles ranging in size from several nanometers (e.g., from about 10 nanometers) to several micrometers (e.g., up to 10 micrometers), combinations thereof, or other suitable morphologies to one of skill in the art.

The methods of the disclosure are advantageous over traditional methods of co-crystal formation because they do not require a liquid solvent. The liquid solvent-free conditions of the methods disclosed herein allows circumvention of the fundamental problems associated with traditional co-crystal formation (e.g., formation via high energy grinding or precipitation from an evaporating solvent), such as conversion back into their components, and does not dictate that the resulting co-crystals exist in a powder or aggregate of individual crystals. The present methods and apparatuses can be used in applications that are incompatible or not preferably performed in the presence of a solvent or liquid. For example, seeds can be coated without using liquid prior to planting to prevent premature gestation and/or spoilage. Other effects can be achieved, such as the growth of the plant without the need for genetic modification. See Gray, American Journal of Botany, 44(8), 674 (1957). Coatings of pesticide or antibacterial compounds are also contemplated herein, such as benzylideneacetone which can prevent plants from being eaten by pests or damaged by bacteria during their lifetime. See Ji et al., FEMS Microbiology Letters, 239(2), 241-248 (2004). Coatings in the food industry are contemplated herein, as well, such as for confectionaries, seasonings, glazes, etc. The methods and apparatuses disclosed herein, such as organic vapor co-crystallization ("OVCC"), enable greater control over the properties of coatings. Co-crystals allow for precise tuning of solubility and other physicochemical properties, a higher level of sweetness can be achieved via enhanced dissolution, without increasing the caloric value. See Wang et al., Crystal Growth & Design, 15(6), 2574-2578 (2015). Coatings, such as films, in the medical industry also are contemplated herein, such as coatings (e.g., films) for a stent, needle, microneedle, probe, syringe, cannula, catheter, sponge, clip, mesh, bandage, gauze, dressing, tape, swab, burn dressing, staple, implant, contact lens, medical tubing, adhesive patches, artificial tissue, intraocular lens, endoscopic device, punctal plugs, buccal patches, lingual patches, sub-lingual patches, electrode patches, combinations thereof, or other suitable medical devices to those skilled in the art.

In particular, the methods described herein involve subliming and/or evaporating an organic compound via organic vapor co-crystallization ("OVCC") and one or more co-crystal formers ("coformers") each into a vapor, mixing the vapors together, and jetting the gas mixture onto a substrate, where the organic compound and one or more coformers condense to form a co-crystal. By using OVCC to produce co-crystals, instead of traditional methods, films and coatings of co-crystals can be produced directly on a variety of surfaces and objects of different geometries for the first time. Depositing co-crystals on substrates has a broad range of applications—medical, agricultural, and in the food sciences, for example. Coatings on commercially available medical devices opens the path to new and less invasive treatment options. Such medical devices generally have strict requirements in terms of surface uniformity, compound dosage, and sterility, all of which can be easily controlled through the OVCC process. In some embodiments, medical devices that are coated using the methods described herein include a stent, needle, microneedle, probe, syringe, cannula, catheter, sponge, clip, mesh, bandage, gauze, dressing, tape, swab, burn dressing, staple, implant, contact lens, medical tubing, adhesive patches, artificial tissue, intraocular lens, endoscopic device, punctal plugs, buccal patches, lingual patches, sub-lingual patches, electrode patches, combinations thereof, or other suitable medical devices to those skilled in the art.

Coating medical devices with the co-crystals described herein using methods described herein is highly advantageous. Coating a stent inserted into an artery with a drug that treats high cholesterol and triglyceride levels, such as atorvastatin (Lipitor), for example, improves the efficacy of the overall system in clearing arterial blockage. Furthermore, the co-crystals described herein can be tuned to exhibit an immediate release or a controlled release profile of an API by varying the solubility of the co-crystal under physiological conditions. Additional control of release can be achieved by generated a multi-layer co-crystal structure having an inactive a co-crystal barrier layer separating co-crystal active layers containing an API. Upon the degradation (e.g. hydrolysis) of the co-crystal barrier layer, the active ingredient is exposed to the surrounding medium and released rapidly, enhancing the degree to which control of amount of drug released, the rate of release, and the time of release can be achieved independently. As another example, coating a needle or microneedle patch prior to insertion into the skin, rather than direct injection, provides a new route of treatment that does not require deep insertion, alleviating patient discomfort. In contrast, prior coatings of pharmaceutical compounds on microneedles (e.g., non-co-crystal coatings) have been shown to fail in rapidly delivering the pharmaceutical compound to the skin (see Gill, et al., Journal of Controlled Release, 117(2):227-337 (2007)), further highlighting the benefits achievable using the methods and technologies described herein. As a further example, coatings of co-crystals containing anti-inflammatory or anti-microbial compounds (e.g., prednisolone, cefuroxime, or moxifloxacin in the form of a co-crystal) on a medical device, such as an intraocular lens, can improve the reduction in post-operative infection or immunoresponse. In contrast, when such compounds are dosed as traditional eyedrops, there can be challenges, including flushing out by the tear film, variability in dosing, and patient non-compliance with the regimen. When such compounds are injected into the vitreous, serious retinal complications may arise in a limited number of cases. See, e.g., Miyake et al., Nature Scientific Reports (2019) 9:9745. Compounds that are included as a component of the intraocular lens, such as the co-crystals disclosed herein, for example, can allow containment of the drug inside the lens bag, followed by elution of the drug into its surrounding aqueous environment, limiting retinal complications.

The methods and aparratuses for forming co-crystals described herein can be designed to achieve personalization of dosage, with respect to composition, amounts, as well as timing and spatial distribution of release of the active or passive ingredients of a drug, and/or release of diagnostic ingredients (see Kuminek et al., Adv. Drug Deliv. Rev., 2017, for co-crystal fine tuning). In some embodiments, the methods can be tuned to allow for the delivery of the desired ingredients at a desired time, to the desired target by controlling release rate and frequency, as well as concentration. For example, depositing the co-crystal onto a substrate with a thin metal strip allows the use of electrical current on this metal strip to melt the cocrystal at a temperature lower than the pure compound. A patch containing such a system is useful for delivering medication dermally. In this manner, digitally-controlled delivery of topical anaesthetics, anti-inflammatories, anti-microbials, or combinations thereof is enabled. Another example includes depositing a co-crystal onto a dissolvable substrate, such as a pullulan film, followed by folding or rolling of the film to achieve a layered system that sequentially releases the co-crystallized active ingredient, modulated by the time required to dissolve the pullulan film. Other examples of dissolvable, biocompatible films include polycaprolactone (PCL), PLGA, PLA, and others. Vapor deposition of polymer films, such as parylene C and related derivatives, onto co-crystalline films achieves a similar layered system functionality.

The co-crystals disclosed herein can be formed as coatings, such as films, on the substrate, as previously described. The coatings and films can be used to produce other forms of the co-crystals, such as a powder, e.g. by scraping, shaking, blowing, brushing, or spalling the coating or film off the substrate. OVCC expands the capabilities of co-crystal systems, which are currently limited in both application and manufacturability. It is important to note that there are currently no marketed co-crystal drug products, partly due to low manufacturability and reproducibility. Current literature regarding co-crystal systems comes from labs that produce these systems in small quantities and under conditions that do not scale well to industrial production. OVCC, in contrast, incorporates readily controlled process parameters amenable to automation, as well as hardware amenable to production scale-up, enabling high throughput and high precision manufacturing of co-crystal products.

The co-crystals disclosed herein can be coated onto a substrate in one or more layers. In embodiments, the co-crystals can be coated onto a substrate in a single layer, or two layers, or three layers, or four layers, or more. For example, a first layer of co-crystals can be coated directly onto a substrate, and a second layer of co-crystals can be coated atop the first layer of co-crystals. The first layer of co-crystals and the second layer of co-crystals can comprise the same composition of co-crystals or a different composition of co-crystals. Further, a first layer of co-crystals can be coated directly onto a substrate and a second layer of another substance, such as a polymer film or another vapor-deposited material, e.g., ibuprofen, paracetamol, tamoxifen, parylene-C, parylene-N, combinations thereof, or other material suitable to one of ordinary skill in the art, can be layered on top of the first layer of co-crystals. In some embodiments, a third layer, of co-crystals, can be coated atop the second layer of another substance or a second layer of co-crystals. In embodiments wherein the substrate is coated with multiple layers of co-crystals, each layer can have the same thickness or different thicknesses. In embodiments wherein the substrate is coated with multiple layers or co-crystals, each layer can have the same concentration of co-crystal or differenct concentrations of co-crystal. In embodiments wherein the substrate is coated with multiple layers or co-crystals, each layer can have co-crystals of the same composition or co-crystals of differing compositions, such as a first layer of caffeine and succinic acid co-crystals and a second layer of indomethacin and saccharin co-crystals (having anti-inflammatory and sweetening properties, respectively), ibuprofen and nicotinamide co-crystals, or others suitable to one of ordinary skill in the art. Thus, provided herein are methods and apparatuses for forming a single co-crystal coating onto a substrate. Also provided herein are methods and apparatuses for forming multiple layers of co-crystals onto a substrate.

OVCC is different from previously known organic vapor phase deposition ("OVPD") or organic vapor jet printing ("OVJP") technologies in that in OVCC the ratio of the organic compound to one or more coformers, the two (or more) have a closer molar ratio (e.g., 5:1 to 1:5, 3:1 to 1:3, 2:1 to 1:2, 1.5:1 to 1:1.5, or 1:1) than the two components used in, for example, a doped emissive layer of an organic light emitting device ("OLED") (e.g., 1:10 or lower are typical molar ratios but not in a co-crystallized morphology). Moreover, in most instances of co-depositing two or more materials from the vapor phase, the result is commonly a disruption of molecular packing that creates an amorphous or, even if crystallization is achieved, it is in the form of a phase-separated layer. In contrast, OVCC allows a co-crystal film that exhibits a crystalline lattice configuration. Furthermore, films produced by OVJP that include two or more components have not been shown to form co-crystals, as does the OVCC technique described herein. Recently, OVJP was used to deposit coatings of pharmaceutical compounds, maintaining their chemical structure and biological activity. See Shalev et al. Nature Communications, 8(1), 711 (2017). The resulting drug films showed distinct micro- or nano-crystalline morphology, which allows for an increase in dissolution rate as compared to the bulk powder form of the drug, primarily due to the higher effective surface area resulting from the smaller particle size. The drug films were shown to maintain the same molecular packing and chemical composition before and afterdepositing as confirmed by X-ray diffraction ("XRD") and Fourier-transform infrared spectroscopy ("FTIR") analysis. See Shalev et al. Because of the enhanced dissolution rate of the drug films, an in vitro test involving human cancer cells showed that these films yielded better or comparable results in limiting cancer cell growth, as compared to the bulk powder drug dissolved in both water and organic solvent.

OVCC methods as disclosed herein allow for control over particle size and distribution based on choice of, and ability to control, various process parameters, such as substrate temperature, carrier gas flow rate, nozzle seperation, and source temperature. Control of substrate temperature is important, because a lower temperature limits crystal growth following nucleation, allowing for control over the range of particle size. Current methods to create co-crystals do so in solution, resulting in a powder or aggregate of individual crystals upon drying. Using OVCC, films and coatings of co-crystals can be produced directly and on a variety of surfaces and objects of different geometries, which has a broad range of applications even beyond the pharmaceutical field.

Methods of Forming Co-Crystals

Provided herein are methods of forming a co-crystal of an organic compound and a coformer comprising: (a) subliming and/or evaporating the organic compound optionally in the presence of an organic compound carrier gas to form a organic compound vapor; (b) subliming and/or evaporating the coformer optionally in the presence of a coformer carrier gas to form a coformer vapor; (c) mixing the organic compound vapor and the coformer vapor, optionally in the presence of a mixing gas, to form a vapor mixture, and (d) condensing the vapor mixture onto a substrate to form the co-crystal. In embodiments, the organic compound and coformer are sublimed. In embodiments, the organic compound and coformer are evaporated. In embodiments, the organic compound is sublimed and the coformer is evaporated. In embodimetns, the organic compound is evaporated and the coformed is sublimed.

The methods provided herein can comprise an organic compound that is between 100 and 5000 g/mol. In embodiments, the organic compound can be between approximately 100 and 1000 g/mol, for example, about 100 g/mol, about 150 g/mol, about 200 g/mol, about 250 g/mol, about 300 g/mol, about 400 g/mol, about 500 g/mol, about 600 g/mol, about 700 g/mol, about 800 g/mol, or about 900 g/mol. In some cases, the organic compound of the disclosure herein can have a vapor pressure of $10^{-3}$ Pascals to $10^6$ Pascals, such as, $10^{-2}$ Pascals to $10^5$ Pascals, or 1 Pascals to $10^4$ Pascals.

In some cases, the organic compound can comprise an active pharmaceutical ingredient ("API"). In embodiments, the API can comprise a compound selected from the group consisting of caffeine, carbamazepine, 5-methoxy sulfadiazine, ethenzamide, nalidixic acid, isoniazid, furosemide, sulfadimidine, celecoxib, temozolamide, piroxicam, tryptamine, chlorzoxazone, p-coumaric, itraconazole, fluoxetine, telaprevir, sildenafil, theophylline, aceclofenac, 5-nitrouracil, indomethacin, aripiprazole, and atorvastatin, or a mixture thereof. In embodiments, the API can be an antibiotic. For example, a co-crystal comprising an antibiotic API can be deposited onto a catheter to prevent urinary tract infections brought on by a catheter. In embodiments, the API can be an antimicrobial. For example, a co-crystal comprising an antimicrobial API can be deposited onto a bandage. In embodiments, the API can be a topical analgesic. For example, a co-crystal comprising a topical analgesic, such as a fast-acting topical analgesic, can be deposited onto needles.

In some cases, the organic compound is not an API. In various embodiments, the organic compound can comprise an agricultural and/or food industry-relevant compound. In some cases, the organic compound can comprise a pesticide, antibacterial, confectionary, seasoning, glaze or a mixture thereof. Some contemplated non-API organic compounds useful in the methods described herein include gibberellin, benzylideneacetone, and acesulfame.

In some cases, the organic compound exhibits strong optical absorption and/or luminescence, and can be used as an indicator of dissolution, a tracer for authentication purposes, other purposes known to those of ordinary skill in the art, or combinations thereof.

As used herein, the term "coformer" refers to a non-charged molecule that can cocrystallize with the organic compound. In embodiments, the coformer has a molecular weight that is within a range of about 200 g/mol of the organic compound's molecular weight, the coformer and the organic compound are about integer mulitples of each other by mole ratio, and the coformer can associate with the organic compound, such as, through hydrogen bonding, van Der Waals interactions, or electrostatic interactions. In embodiments, the coformer can comprise at least one functional group capable of hydrogen bonding to the organic compound of the co-crystal. In some embodiments, the coformer can comprise a carboxylic acid, ketone, alcohol, aldehyde, amide, amine, heterocycle comprising at least one N or O ring atom, or combinations thereof. In various embodiments, the coformer can comprise a pyridine, carboxylic acid, or amine. In some cases, the method can comprise from one to ten different coformers, for example, one, two, three, four, five, six, seven, eight, nine, or ten. In embodiments, the coformer can be selected from the group consisting of benzoic acid, oxalic acid, malonic acid, succinic acid, maleic acid, fumaric acid, glutaric acid, adipic acid, pimelic acid, 3,5-dihydroxybenzoic acid, triflouroacetic acid, 2,5-dihydroxybenzoic acid, 2,4-dihydroxybenzoic acid, m-nitrobenzoic acid, 5-chlorosalicylic acid, saccharin, citric acid, tartaric acid, 2,3-dihydroxybenzoic acid, 3,4-dihydroxybenzoic acid, barbital, 4-hydroxybenzoic acid, 1-hydroxy-2-naphthoic acid, malic acid, 3-hydroxybenzoic acid, 6-hydroxy-2-naphthoic acid, methylgallate, salicyclic acid, 2-hydroxybenzoic acid, formic acid, 3-hydroxy-2-naphthoic acid, sulfacetamide, acetic acid, sulfaproxyline, sulfuric acid, sulfamic acid, ethylenediamine, octadecylamine, glucono-delta lactone, allocitric acid, sucralose, indole, 1-hydroxyethyldene-1,1-diphosphonic acid, skatole, 5-chlorosalicylic acid, urea, 5-nitroisophthalic acid, trimesic acid, gentisic acid, ketoglutaric acid, adamantine tricarboyxlic acid, t-butylhydroquinone, isocirtric acid, trifluoroethanol, camphoric acid, 4-aminobenzoic acid, 2,6-pyridinedicarboxylic acid, aspirin, butyric acid, formamide, nicotinamide, nitromethane, 1,4-benzoquinone, glycolic acid, terephtalaldehyde, dioxane, N-methylpyrrolidone, dimethylsulfoxide, dimethylacetamide, acetone, dimethylformamide, furfural, and 4,4'-bipyridine, or a mixture thereof. In some cases, the coformer can be selected from the group consisting of benzoic acid, oxalic acid, succinic acid, maleic acid, trifluoroacetic acid, formic acid, acetic acid, salicyclic acid, urea, formamide, aspirin and sucralose. In embodiments, the coformer is succinic acid or aspirin.

In various cases, the co-crystal can comprise one or more coformers.

The methods provided herein can comprise subliming and/or evaporating the organic compound to form an organic compound vapor. In some cases, the organic compound is sublimed and/or evaporated at a temperature that is 1° C. to 300° C. above its onset of sublimation and/or evaporation, as determined by thermogravimetric analysis ("TGA"), for example, 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 25° C., 30° C., 35° C., 40° C., 45° C., 50° C., 60° C., 70° C., 80° C., 90° C., 100° C., 150° C., 200° C., 250° C., or 300° C. above its onset of sublimation. In some cases, the organic compound is sublimed and/or evaporated at a temperature that is 5° C. to 150° C., 10° C. to 100° C., or 10° C. to 50° C. above its onset of sublimation, as determined by TGA. In some cases, the organic compound vapor is near saturation. In embodiments, the organic compound vapor is saturated. In some embodiments, the organic compound vapor is supersaturated. In various cases, the organic compound vapor is in the presence of an organic compound carrier gas.

An organic compound carrier gas can comprise an inert gas (e.g., nitrogen, argon, $CO_2$, etc.) or a reactive gas (e.g. HCl, $H_2O$, $O_3$, $CH_4$, $O_2$ etc.). In some cases, the organic compound carrier gas can comprise nitrogen, carbon dioxide, krypton, argon, hydrogen, helium, oxygen, water, methane, nitrous oxide or a mixture thereof. In some cases, the organic compound carrier gas has a flow rate of about 1 to 500 standard cubic centimeters per minute ("sccm"). In embodiments, the organic compound carrier gas can have a flow rate of about 1 to 200 sccm, such as, about 1 to 150 sccm, about 1 to 100 sccm, about 1 to 50 sccm, or about 25 to 50 sccm, for example, 1 sccm, 5 sccm, 10 sccm, 15 sccm, 20 sccm, 25 sccm, 30 sccm, 35 sccm, 40 sccm, 45 sccm, 50 sccm, 60 sccm, 70 sccm, 80 sccm, or 90 sccm. In various embodiments, the organic compound carrier gas can carry the organic compound to a mixing chamber prior to step (c).

In the methods disclosed herein, the coformer can be sublimed and/or evaporated at a temperature that is 1° C. to 300° C. above its onset of sublimation and/or evaporation, as determined by thermogravimetric analysis ("TGA"), for example, 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 25° C., 30° C., 35° C., 40° C., 45° C., 50° C., 60° C., 70° C., 80° C., 90° C., 100° C., 150° C., 200° C., 250° C., or 300° C. In some cases, the coformer is sublimed and/or evaporated at a temperature that is 5° C. to 150° C., 10° C. to 100° C., or 10° C. to 50° C. above its onset of sublimation and/or evaporation, as determined by TGA. In some cases, the coformer vapor is near saturation. In embodiments, the coformer vapor is saturated. In some embodiments, the coformer vapor is supersaturated. In various cases, the coformer vapor is in the presence of a coformer carrier gas.

The coformer carrier gas can comprise an inert gas (e.g., nitrogen, argon, $CO_2$, etc.) or a reactive gas (e.g. HCl, $H_2O$, $O_3$, $CH_4$, $O_2$ etc.). In embodiments, the coformer carrier gas can comprise nitrogen, carbon dioxide, krypton, argon, hydrogen, helium, oxygen, water, methane, nitrous oxide or a mixture thereof. In some cases, the coformer carrier gas has a flow rate of about 1 to 500 standard cubic centimeters per minute ("sccm"). In embodiments, the coformer carrier gas can have a flow rate of about 1 to 200 sccm, such as, about 1 to 150 sccm, about 1 to 100 sccm, about 1 to 50 sccm, or about 25 to 50 sccm, for example, 1 sccm, 5 sccm, 10 sccm, 15 sccm, 20 sccm, 25 sccm, 30 sccm, 35 sccm, 40 sccm, 45 sccm, 50 sccm, 60 sccm, 70 sccm, 80 sccm, or 90 sccm. In various embodiments, the coformer carrier gas can carry the coformer to a mixing chamber prior to step (c). In some embodiments, the organic vapor and coformer carrier gas are focused in the form of a jet, so as to produce a pattern of deposited material on the surface. In some embodiments, the organic vapor and coformer carrier gas are shaped to produce a curtain flow.

The methods provided herein of forming a co-crystal can comprise mixing the organic vapor mixture and the coformer vapor mixture to form a vapor mixture. In embodiments, the vapor mixture can comprise a molar ratio of the organic compound and the coformer of 100:1 to 1:100, for example, 1:1, 1:1.1, 1:1.3, 1:1.5, 1:2, 1:3, 1:4, 1:5, 1:6, 1:7,1:8, 1:9, 1:10, 1:15, 1:20, 1:30, 1:40,1:50, 1.1:1, 1.3:1, 1.5:1, 2:1, 3:1, 4:1, 5:1, 6:1, 7:1, 8:1, 9:1, 10:1, or 15:1. In some embodiments, the vapor mixture can comprise a molar ratio of the organic compound and the coformer of 10:1 to 1:10, or 1:1 to 1:10, or 1:1 to 1:8, or 1:1 to 1:6, or 1:1 to 1:5, or 1:3 to 1:5, 2:1 to 1:1, or 1:1.1 to 1:1.5, or 5:1 to 1:5, or 3:1 to 1:1, 2:1 to 1:1, or 1.1:1 to 1.5:1. In some embodiments, the vapor mixture can comprise more than one coformer, for example, one, two, three, four, or five different coformers. In embodiments wherein the vapor mixture comprises more than one coformer, the vapor mixture can comprise a molar ratio of the organic compound to the total coformer (wherein total coformer=coformer 1+coformer 2+coformer x, where x can be 0, 1, 2, or 3) of 100:1 to 1:100, for example, 1:1, 1:1.1, 1:1.3, 1:1.5, 1:2, 1:3, 1:4, 1:5, 1:6, 1:7, 1:8, 1:9, 1:10, 1:15, 1:20, 1:30, 1:40, 1:50, 1.1:1, 1.3:1, 1.5:1, 2:1, 3:1, 4:1, 5:1, 6:1, 7:1, 8:1, 9:1, 10:1, or 15:1. In some embodiments, the vapor mixture can comprise a molar ratio of the organic compound and the total coformer of 10:1 to 1:10, or 1:1 to 1:10, or 1:1 to 1:8, or 1:1 to 1:6, or 1:1 to 1:5, or 1:3 to 1:5, 2:1 to 1:1, or 1:1.1 to 1:1.5, or 5:1 to 1:5, or 3:1 to 1:1, 2:1 to 1:1, or 1.1:1 to 1.5:1.

In some cases, the organic compound vapor and the coformer vapor of step (c) are in the presence of a mixing gas. In embodiments, the mixing gas can comprise an inert gas (e.g., nitrogen, argon, $CO_2$, etc.) or a reactive gas (e.g. HCl, $H_2O$, $O_3$, $CH_4$, $O_2$ etc.). In embodiments, the mixing gas can comprise nitrogen, carbon dioxide, krypton, argon, hydrogen, helium, oxygen, water, methane, nitrous oxide or a mixture thereof. In some cases, the mixing gas comprises nitrogen. In some embodiments, the mixing gas can have a flow rate of about 1 to 500 standard cubic centimeters per minute ("sccm"). In embodiments, the mixing gas can have a flow rate of about 1 to 200 sccm, such as, about 1 to 150 sccm, about 1 to 100 sccm, about 1 to 50 sccm, or about 25 to 50 sccm, for example, 1 sccm, 5 sccm, 10 sccm, 15 sccm, 20 sccm, 25 sccm, 30 sccm, 35 sccm, 40 sccm, 45 sccm, 50 sccm, 60 sccm, 70 sccm, 80 sccm, or 90 sccm. In various embodiments, the mixing gas carries the vapor mixture to the substrate.

In some cases, the method provided herein can further comprise exposing the mixing gas to a guard flow gas prior to step (d), such that the guard flow gas surrounds the mixing gas, and the mixing gas comprises the vapor mixture. In some embodiments, the guard flow gas comprises nitrogen, carbon dioxide, kypton, argon, hydrogen, helium, methane, nitrous oxide, or a mixture thereof. As used herein, the term "guard flow gas" refers to a gas that substantially surrounds the jetstream carrying the vapor mixture. The guard flow gas can be used to protect the mixing gas comprising the vapor mixture from other gases that may react with the vapor mixture, and/or protect the area of the substrate where the co-crystals are deposited.

The methods provided herein comprise condensing the vapor mixture onto a substrate to form the co-crystal. In embodiments, the method herein can further comprise moving the vapor mixture over the substrate during step (d). In some embodiments, the nozzle 350 (FIG. 1) can be rastered over the substrate such that the vapor mixture moving over the substrate. In some embodiments, the nozzle 350 can be rastered keeping the center to center line spacing from 0.01 mm to 100 mm, such as, 0.01 mm, 0.05 mm, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm. In various embodiments, the nozzle 350 can be rastered such that the raster velocity is from 0.01 mm/s to 100 mm/s. In some embodiments, the raster velocity is from 0.01 mm/s to 10 mm/s, for example, 0.01 mm/s, 0.05 mm/s, 0.1 mm/s, 0.2 mm/s, 0.3 mm/s, 0.4 mm/s, 0.5 mm/s, 0.6 mm/s, 0.7 mm/s, 0.8 mm/s, 0.9 mm/s, 1 mm/s, 2 mm/s, 3 mm/s, 4 mm/s, 5 mm/s, 6 mm/s, 7 mm/s, 8 mm/s, 9 mm/s, or 10 mm/s. In some cases, the method can further comprise moving the substrate under the vapor mixture during step (d).

In some embodiments, the substrate is at room temperature, about 20-25° C. In some cases, the substrate can be temperature-controlled. In embodiments, the substrate can be at a temperature of −100° C. to 100° C., for example, −90° C., −80° C., −70° C., −60° C., −50° C., −40° C., −30° C., −20° C., −10° C., −5° C., 0° C., 5° C., 10° C., 15° C., 20° C., 25° C., 30° C., 35° C., 40° C., 45° C., 50° C., 55° C., 60° C., 65° C., 75° C., 80° C., 85° C. , 90° C., or 95° C. In some cases, the substrate can be at a temperature of −50° C. to 50° C., such as, 5° C. to 25° C.

The substrate can be made of any material that one of skill in the art would find suitable to coat with the co-crystals. In embodiments, the substrate can comprise metal, plastic, wood, ceramic, quartz and other silicon based materials, glass, paper, composites, semiconductors, fabric, dissolvable polymer sheets/films, small molecular films (a layer of, e.g., food dye or fluorescent dye that could act as a tracer to signal dissolution of a particular layer), biofilms, or the like, or a mixture thereof. In embodiments, the substrate can comprise quartz, glass, metal, plastic, ceramic or a combination thereof. In various cases, the substrate can comprise a medical device. In various cases, the medical device is selected from the group consisting of a stent, needle, microneedle, probe, syringe, cannula, catheter, sponge, clip, mesh, bandage, gauze, dressing, tape, swab, burn dressing, staple, implant, contact lens, medical tubing, adhesive patches, artificial tissue, intraocular lens, endoscopic device, punctal plugs, buccal patches, lingual patches, sub-lingual patches, electrode patches, and combinations thereof. In various cases, the medical device is a stent, needle, a sponge, or an intraocular device. In various cases, the substrate can comprise a plant seed. In some embodiments, the substrate can comprise artificial tissue. In some embodiments, the substrate is coated with the co-crystal during step (d) above.

Co-Crystals Formed Using OVCC

Provided herein are co-crystals produced by the disclosed methods. In embodiments, the co-crystals comprise an organic compound associated with a coformer. As previously described herein, the organic compound can associate with the coformer via hydrogen bonding, van Der Waals interactions, or electrostatic interactions. In embodiments, the co-crystals comprise hydrogen bonded organic compound and coformer. In embodiments, the co-crystal can comprise the organic compound and the coformer in a molar ratio of 1:5 to 5:1. In some cases, the cocyrstal can comprise the organic compound and the coformer in a ratio of 1:3 to 3:1, such as, 1:2 to 2:1, 1:1.5 to 1.5:1, 1:1.2 to 1.2:1, 1:1 to 2:1, 1:2 to 1:1, for example, 1:1, 1:2, or 1:3. The co-crystal produced by the disclosed methods are stable at 25° C., characterized by differential scanning calorimetry, microscopy, X-ray diffraction, or a combination thereof. As used herein, the term "stable co-crystal" refers to a co-crystal that retains its crystalline structure after storage at about 25° C., 1 atm, and a relative humidity of 40-50% in open air for at least 24 hours, characterized by X-ray diffraction ("XRD") as described herein.

In embodiments, the co-crystals can comprise co-crystals known and/or suitable to one of skill in the art. Contemplated co-crystals that are known can be used herein, such as those in the following references: Qiao et al., Int J Pharm, 2011 Oct. 31; 419(1-2):1-11; Kuminek et al., Adv Drug Deliv Rev., 2016 Jun. 1; 101:143-166; Shan N, Zaworotko M J. *Drug Discov. Today* 2008, 13 440; Schultheiss N, Bethune S, Henck J-O., *CrystEngComm* 2010, 12, 2436; Bolton O, Matzger A J. *Angew Chemie Int Ed.* 2011, 50, 8960; Friščić T, Jones W., *Cryst. Growth Des.* 2009, 9, 1621; Karimi-Jafari M, Padrela L, Walker G M, Croker D M., *Cryst. Growth Des.* 2018, 18, 6370.

Co-crystals that can be used in the method described herein are determined by several qualities: the co-crystals must be 1) crystalline, 2) the two or more components of the co-crystal (i.e., organic compound and coformer) must be stabilized by hydrogen bonding or other non-valency intermolecular interactions (e.g., van der Waals, π-π interactions, etc.), and 3) the two or more components are, each individually, capable of subliming and/or evaporating at a given temperature without decomposing. Selecting suitable pairs of organic compounds and coformers to form the co-crystals using the methods described herein is well within the knowledge of those skilled in the art. See, e.g., Kuminek et al., Adv Drug Deliv Rev. 2016 Jun. 1; 101: 143-166. For example, the skilled person is aware of compounds (e.g., organic compounds and coformers, as defined herein) that are known to form co-crystals, and how to obtain the evaporation properties of those compounds. The skilled person can then tune the evaporation conditions (e.g., temperature, overpressure, flow) to result in the levels of vapor pressure appropriate for forming the co-crystals on substrates using the methods described herein.

The co-crystals described herein can be deposited onto a substrate, wherein the co-crystal forms a single coating or film that has a thickness from 1 nm to 10 mm, or multiple layers of coatings or films, each having a thickness from 1 nm to 1 mm. In embodiments, each co-crystal coating can be from 10 nm to 1 mm, such as from 100 nm to 1 mm, 500 nm to 0.1 mm, or 500 nm to 0.01 mm. A variety of coformers can be employed to yield various co-crystals of the same organic compound but the co-crystals having the same organic compound but different coformers may have different solubility advantages. The different solubility advantages can be applied to meet the specific need of a desired application. It is also understood that these coatings need not be dense coatings, but can consist of particles having voids, such as crystallites, needles, flakes, etc.

Co-crystals of caffeine have been widely researched and are relatively well-known. See Trask et al. Crystal Growth & Design, 5(3):1013-1021 (2005). Although caffeine readily forms co-crystals with a wide array of dicarboxylic acids (e.g., oxalic, maleic, malonic, and glutaric acids) when combined using both neat grinding and solvent-drop addition techniques, previous attempts at forming stable co-crystals of caffeine and succinic acid using the traditional techniques failed. See Trask et al. Without being bound by any particular theory, co-crystals of caffeine and succinic acid that are formed using the traditional techniques convert back to the two components too quickly. Using the methods and apparatuses described herein, however, stable co-crystals of caffeine and succinic acid were able to be formed for the first time.

Thus, provided herein is a caffeine-succinic acid co-crystal, which is stable at room temperature (e.g., 20-25° C.). The caffeine-succinic acid co-crystals described herein can be characterized by, for example, scanning electron microscopy ("SEM"), X-ray diffraction ("XRD"), and differential scanning calorimetry ("DSC"), each as described in the Examples section below. The caffeine-succinic acid co-crystal comprises caffeine and succinic acid in a molar ratio of about 1:1.

Caffeine crystals, succinic acid crystals, and caffeine-succinic acid co-crystals described herein can be deposited on a substrate to form films with a thickness ranging between about 100 nm and about 1 mm. However, as shown in the SEM image in FIG. 2, and also in FIG. 5, these films need not be dense and can include voids. When pure caffeine and pure succinic acid are each deposited onto a substrate via the vapor jet process, the pure caffeine exhibits a hollow pillar morphology, and the pure succinic acid forms approximately 20 micrometer aggregates that have a branched (ramified) morphology, with short needles and small platelets decorating a branch, see FIG. 5. Further details about SEM characterization of the caffeine-succinic acid co-crystals can be found in the Examples section. The caffeine-succinic acid co-crystal deposits appear as more highly branched "bushes", ranging from 100 to 500 micrometers in size for each aggregate, with individual branches being up to about 5 micrometers in width, with no preferred orientation. See FIG. 5.

The caffeine-succinic acid co-crystals described herein also can be characterized by an XRD pattern comprising peaks at 14, 18, and 22±0.2° 2θ using Cu Kα radiation. In some embodiments, the caffeine-succinc acid co-crystals described herein can be characterized by an XRD pattern substantially as depicted in the top trace of FIG. 3. Further details about XRD characterization of the caffeine-succinic acid co-crystals can be found in the Examples section.

Figure 4:
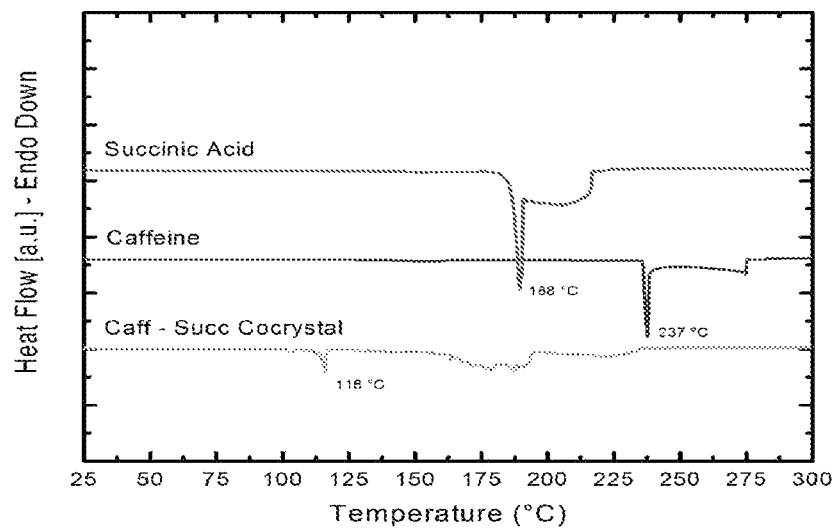
FIG. 4 depicts a differential scanning calorimery ("DSC") thermograph of pure succinic acid (top trace), pure caffeine (middle trace), and a co-crystal of caffeine and succinic acid (bottom trace).

Additionally or alternatively, the caffeine-succinic acid co-crystals described herein can be characterized by DSC. For example, the co-crystal can be characterized by a DSC thermograph having a peak at about 116° C., as shown in FIG. 4. If some residual succinic acid is present in the co-crystal sample, then the DSC thermograph will also show a residual melting event having an onset at about 165° C. In contrast, pure caffeine and pure succinic acid show endotherms around 237° C. and 188° C., respectively, corresponding to their known melting points. In particular, the caffeine-succinic acid co-crystal can be characterized by a DSC thermograph substantially as depicted in FIG. 4. Further details about DSC characterization of the caffeine-succinic acid co-crystals can be found in the Examples section Co-Crystal Compositions Another aspect of the disclosure provides compositions (alternatively referred to as formulations throughout) that include the co-crystals produced by the OVCC methods described herein. Compositions typically include an acceptable carrier. When the composition is a pharmaceutical composition, the carrier is pharmaceutically acceptable. When the composition is a neutraceutical composition, the carrier is neutraceutically acceptable.

The phrase "pharmaceutically acceptable" is employed herein to refer to those ligands, materials, compositions, and/or dosage forms which are, within the scope of sound medical judgment, suitable for use in contact with the tissues and other internal use of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) ethyl alcohol; and (20) other non-toxic compatible substances employed in pharmaceutical formulations. A pharmaceutical carrier can be chosen for a particular co-crystal depending on the carrier's ability to maintain the integrity of the co-crystal before administration of the co-crystal to a subject. For example, a co-crystal should exhibit little to no solubility in its carrier to avoid dissolution of the co-crystal before administration to the subject. In certain embodiments, pharmaceutical compositions provided herein are non-pyrogenic, i.e., do not induce significant temperature elevations when administered to a patient.

A pharmaceutically acceptable salt of the co-crystals disclosed herein can be of a basic moiety on the co-crystal and an acid, or an acidic moiety on the co-crystal and a base. These salts can be prepared by reacting the co-crystal in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, a co-crystal provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a co-crystal provided herein. These salts can likewise be prepared by reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

The concentration of a compound provided herein in a pharmaceutically acceptable composition will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Co-Crystal-Coated Substrates

The OVCC methods described herein are advantageous in that they allow co-crystals to be deposited on substrates, such as medical devices. Previously, depositing co-crystals on such substrates, such as complex co-crystals containing active, passive, and/or diagnostic ingredients, was unattainable when the co-crystals were formed using traditional techniques (e.g., those that require a liquid solvent). Thus, the disclosure also provides substrates that are coated with co-crystals produced using the OVCC methods described herein. The substrates coated with a co-crystal produced by the methods disclosed herein can be made of any material that one of skill in the art would find desirable to coat with the co-crystals described herein. In embodiments, the substrates coated with co-crystals produced using the OVCC methods disclosed herein can comprise metal, plastic, wood, ceramic, quartz and other silicon based materials, glass, paper, composites, semiconductors, fabric, dissolvable polymer sheets/films, small molecular films (e.g., a layer of a food dye or fluorescent dye that could act as a tracer to signal dissolution of a particular layer), biofilms, or the like, or combinations thereof. In embodiments, the substrate can comprise quartz, glass, metal, plastic, ceramic or a combination thereof. In various cases, the substrate can comprise a medical device. In various cases, the medical device is selected from the group consisting of a stent, needle, microneedle, syringe, cannula, catheter, sponge, clip, mesh, bandage, gauze, dressing, tape, swab, burn dressing, staple, implant, contact lens, medical tubing, adhesive patches, intraocular lens, endoscopic device, punctal plugs, buccal patches, lingual patches, sub-lingual patches, electrode patches, and combinations thereof. In various cases, the medical device is a stent, needle, a sponge, or intraocular lens. In various cases, the substrate can comprise an agricultural or food industry relevant substrate. In various embodiments, the substrate can comprise a plant seed. In various embodiments, the substrate can comprise a semiconductor. In embodiments, the substrate can comprise a fabric. In some embodiments, the substrate can comprise a contact lens.

As previously described, depositing co-crystals on substrates has a broad range of applications. For example, coatings on commercially available medical devices can open the path to new and less invasive treatment options, for example, reducing inflammation or reducing infection resk for invasive procedures (e.g., intubation). Such medical devices generally have strict requirements in terms of surface uniformity, compound dosage, and sterility, all of which can be easily controlled through the OVCC process described herein. Thus, the disclosure provides a co-crystal coated medical device.

Coating a semiconductor substrate by the methods described herein is advantageous because the dissolution of the co-crystal exposes the semiconductor, which can be detected via changes in its electrical properties in a circuit. Thus, the disclosure provides a co-crystal-coated semiconductor substrate in which the co-crystal coating is formed using the methods described herein. In embodiments, the semiconductor substrate is coated with a single coating. In embodimetns, the semiconductor substrate is coated with two or more layers of coatings, as previously described herein.

Figure 14:
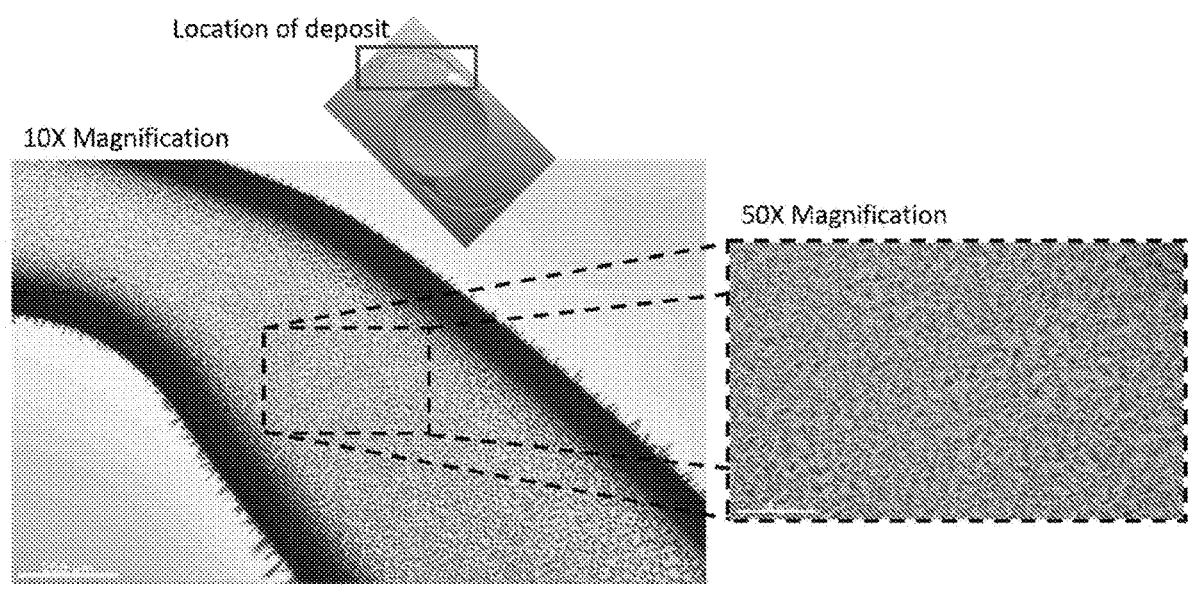
FIG. 14 depicts an intraocular lense coated with a caffeine-succinic acid co-crystals of the disclosure according to the methods and apparatuses described herein.

In some cases, a contact lens substrate can be coated by co-crystals using the methods described herein (see, e.g., FIG. 14). A contact lens coated with an API-containing co-crystal can allow delivery of the API directly to the eye. Thus, the disclosure provides a coated contact lens comprising one or more co-crystalline layers made by the methods described herein. In embodiments, the coated contact lens can comprise two layers of co-crystalline coatings, wherein each layer comprises the same co-crystal. In embodiments, the coated contact lens can comprise two layers of co-crystalline coatings, wherein each layer comprises a different co-crystal.

Figure 6:
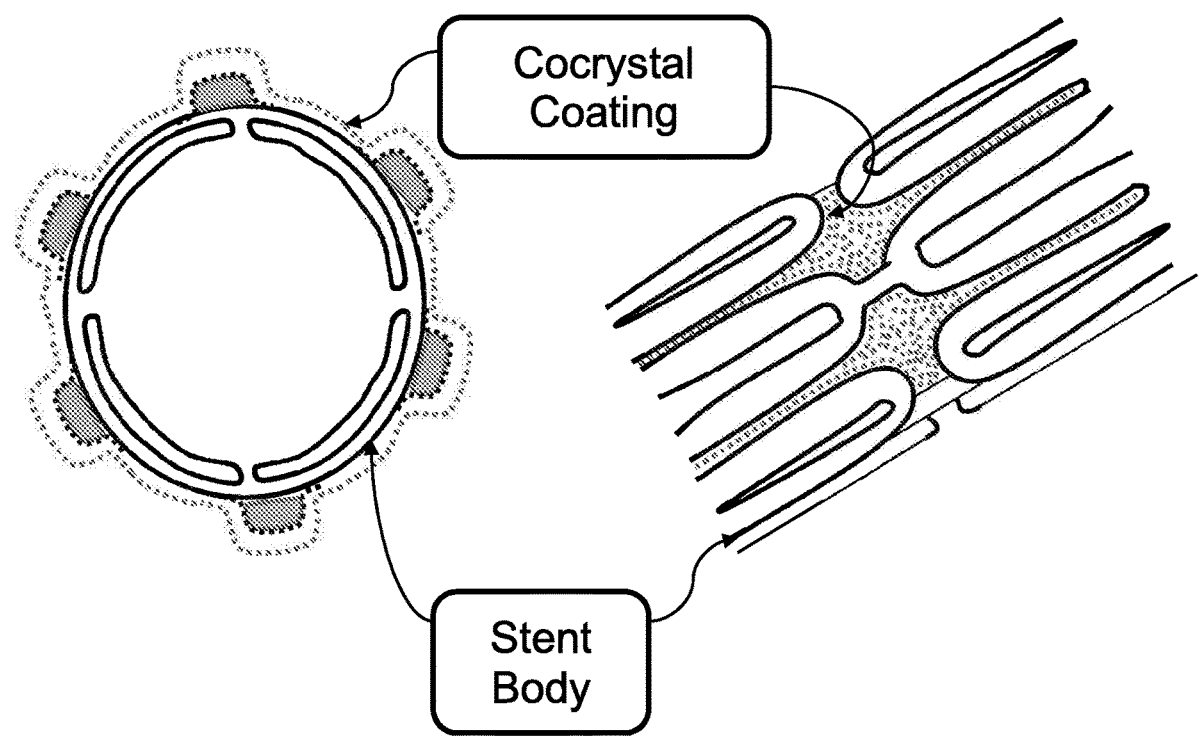
FIG. 6 depicts a schematic of a stent body coated with a co-crystal of the disclosure.

In some embodiments, the disclosure provides a co-crystal-coated stent (see, e.g., FIG. 6). A co-crystal-coated stent can be inserted into an artery with a drug that treats high cholesterol and triglyceride levels, such as atorvastatin (Lipitor), which can improve the efficacy of the overall system in clearing arterial blockage.

Figure 7:
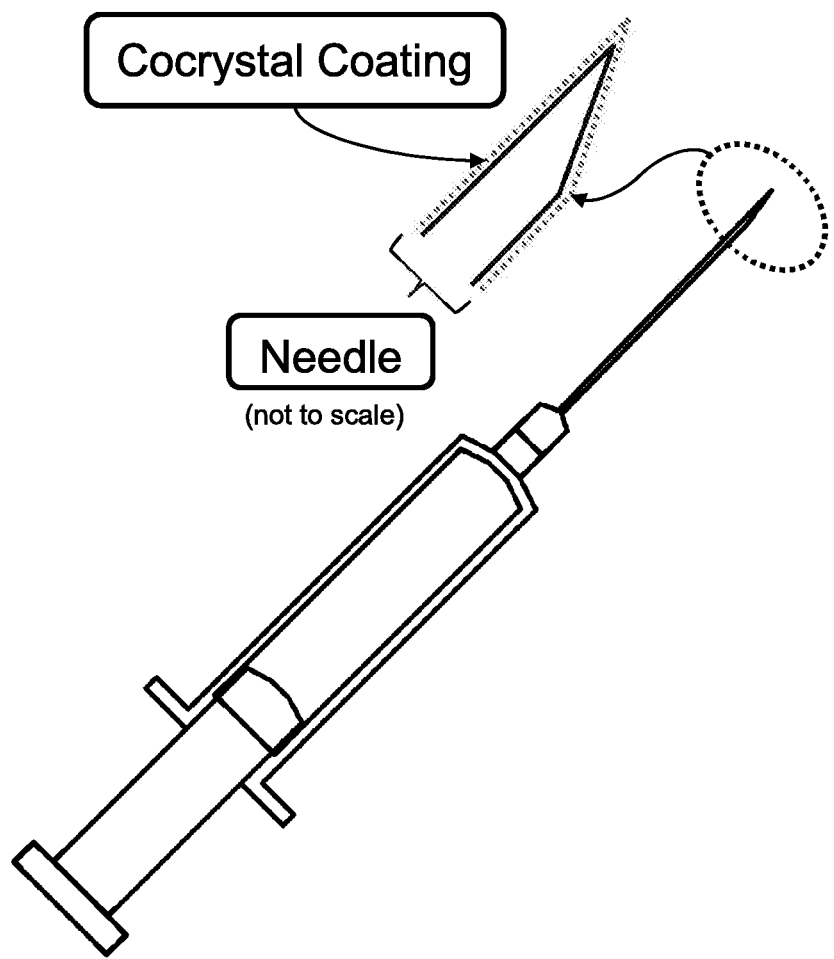
FIG. 7 depicts a schematic of a syringe with the tip coated with a co-crystal of the disclosure.

The disclosure also provides a co-crystal-coated needle (see e.g., FIG. 7). Coating a needle or microneedle patch with a co-crystal prior to insertion into the skin, rather than direct injection, can enable a new route of treatment that does not require deep insertion, alleviating patient discomfort. Thus, the co-crystal coated substrates described herein (e.g., coated needle or microneedles) can allow for smaller needles as modern syringes require penetration into muscle tissue for adequate delivery. Because the co-crystal coating would immediately begin to dissolve upon skin penetration, one would not need to go as deep to achieve this kind of delivery. In contrast, prior coatings of pharmaceutical compounds on microneedles (e.g., non-co-crystal coatings) have been shown to fail in rapidly deliverying the pharmaceutical compound to the skin (see Gill, et al., Journal of Controlled Release, 117(2):227-337 (2007)).

Figure 8:
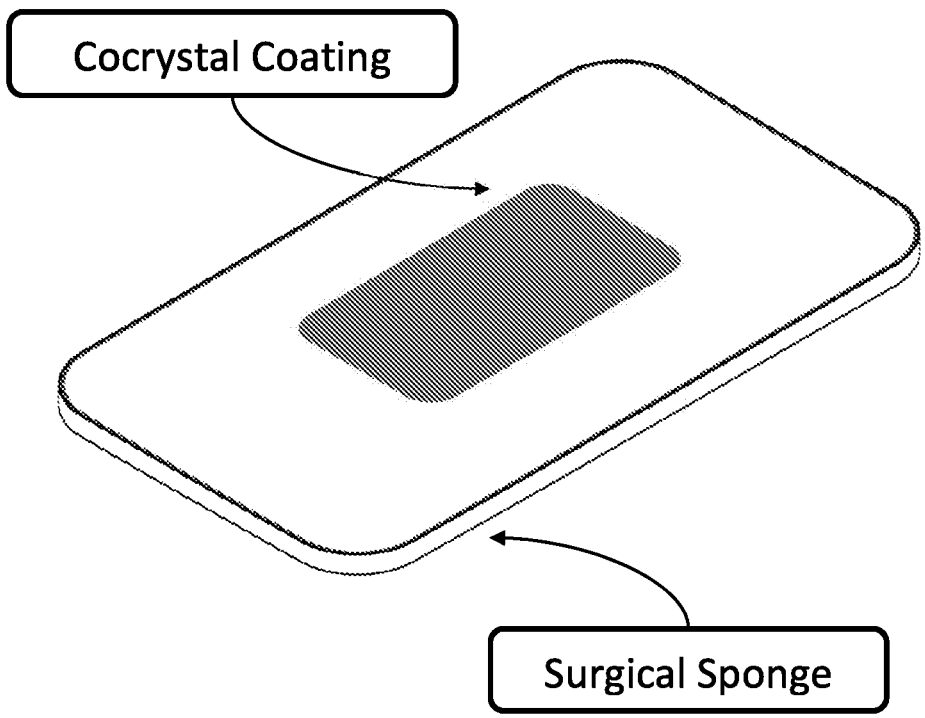
FIG. 8 depicts a schematic of a surgical sponge coated with a co-crystal of the disclosure.

The disclosure further provides a co-crystal coated sponge (see e.g., FIG. 8). Sponges are used in copious quantities during nearly all surgical operations. Having a co-crystal coated on the sponge is useful if the surgeon desires a specific outcome during surgery. For example, a sponge can be coated with a co-crystal antibacterial agent to prevent infection. Another example is a co-crystal coating of an immune suppressant to locally suppress the immune response at the incision site, or a co-crystal anticoagulant to prevent blood clotting.

Figure 9:
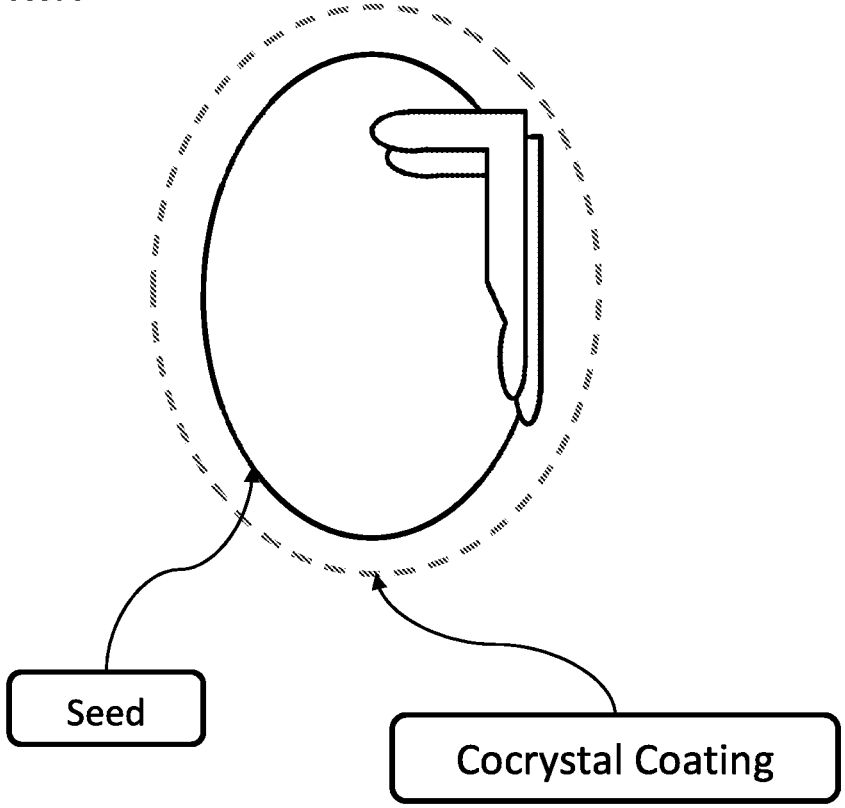
FIG. 9 depicts a schematic of a plant seed coated with a co-crystal of the disclosure.

The disclosure further provides a co-crystal coated plant seed (see e.g., FIG. 9)

Further details about co-crystal coated substrates can be found in the Examples section, below.

Apparatus for the OVCC Formation of Co-crystals

The OVCC process may be performed in an apparatus as disclosed herein. The apparatus can comprise a housing having (i) a vapor mixing chamber adjacent to a jet exiting nozzle end of the housing; and (ii) a receiving end opposite the jet exiting nozzle end; the vapor mixing chamber being adjacent to a temperature control shroud for controlling the temperature of a vapor mixture of the organic compound and the coformer in the vapor mixing chamber; a first tubular internal container for injecting an organic compound and positioned within the receiving end, having (i) an outlet nozzle for feeding the organic compound into the vapor mixing chamber; (ii) a organic compound carrier gas inlet tube; and (iii) a thermocouple at a proximal end for controlling evaporation temperature of the first tubular internal container; and a second tubular internal container for injecting the coformer and positioned within the receiving end, having (i) an outlet nozzle for feeding the coformer into the vapor mixing chamber, (ii) a coformer carrier gas inlet tube, and (iii) a thermocouple at a proximal end for controlling evaporation temperature of the second tubular internal container, wherein at least one of the first tubular container and the second tubular container has a mixing gas inlet. In some cases, the temperature control shroud comprises a heating coil. In some embodiments, the temperature control shroud extends to surround the jet exiting nozzle. In various cases, the apparatus further comprises a guard flow gas inlet positioned for feeding a tertiary gas into the vapor mixing chamber. In various embodiments, the apparatus further comprises a mounting substrate for positioning a target and optionally, a temperature controller for controlling the temperature of the mounting substrate. As used herein the term "tubular internal container" refers to an internal container with a cylindrical shape having a cross-section that is rounded, circular, elliptical, square, rectangular, triangular, or any other curved or polygonal shape. The tubular internal container described herein can have the same cross-sectional dimension along a cylindrical axis, or a varied cross-sectional dimension (e.g,. an hour glass profile) along a cylindrical axis. In some embodiments, the tubular internal container can have a tapered distal and/or proximal end to facilitate operation.

FIG. 1 shows an example of an apparatus for an OVCC process. A co-crystal formation system 300 is formed of a housing 310 surrounded by an optional heating shroud 311. The heating shroud 311 may be an electrically controlled sleeve of a continuous heating surface entirely surrounding a lower portion of the housing cylinder 310. In the illustrated example, the heating shroud 311 is formed of one or more an electrically controlled heating coils surrounding the cylinder 310. The heating shroud 311 extends from a distal portion of housing 310 where a jet existing nozzle 350 is present, up the sides of 310 completely encircling a vapor mixing chamber 307 of the cylinder 310, and extending further up the housing 310 to encircle portions of the housing 310 within which are inserted two injection tubes 320 and 330. The housing 310 may be formed of any suitable material to one of skill in the art, for example, glass. The injection tubes 320 and 330 may be formed of any material suitable to one of skill in the art for example, glass.

In the illustrated example, the injection tube 320 provides the organic compound which is held in an internal container 320-1. The injection tube 330 provides the coformer which is held in an internal container 330-1. The containers 320-1 and 330-1 can be tubular shaped, and can have injection nozzles at their respective distal ends, each injection nozzle injecting its respective organic compound or coformer into the vapor mixing chamber 307.

At the proximal end, the injection tube 320 has temperature regulator, which in this example is a thermocouple 325-1. The injection tube 330 has thermocouple 335-1. The thermocouples 325-1 and 335-1 are monitored by a controller for evaporation temperature in the respective containers 320-1 and 330-1. The injection tubes 320 and 330 also have gas inlet tubes 327-1 and 337-1, respectively.

In operation, carrier gas is injected into the containers 320-1 and 330-1, respectively, through the inlets 327-1 and 337-1, at flow rates Q320 and Q330 as shown. The injected carrier gases, at the initial flow rate, picks up the respective organic compound or coformer vapor from the containers 320-1 and 330-1, carrying it into the vapor mixing chamber 307 by injection through the respective nozzles. In some examples, the carrier gas for the organic compound tube 320 may be diluted by a mixing gas introduced at an inlet 308 prior to the organic compound and the coformer collective entering into the vapor mixing chamber 307. Thus, the carrier gas may be optionally diluted by the dilution gas at a rate $Q_{DIL}$. The rate of injection of API and coformer into the vapor mixing chamber 307 and the timing of the injection of each (the two may be injected simultaneously or asynchronously, at the same injection rate or at different injections rates) depending on desired properties of the resulting co-crystal.

The vapor mixing chamber 307 extends into the jet exiting nozzle 350. In some examples, a shroud 340 is provided surrounding a lower portion of the vapor mixing chamber 307, that shroud 340 providing the capability to inject, through an inlet 309 a guard flow gas a flow rate $Q_{GF}$.

The jet exiting nozzle 350 ejects the vapor mixture of organic compound and coformer onto the substrate 301, where deposition of the co-crystal occurs at 301-1, and the substrate can be optionally positioned on a stationary or movable holder 360, maintained at a temperature $T_{sub}$. Upon exiting the nozzle 350 and approaching the substrate 301-1, the mixture of carrier gas(es) and co-crystal ingredients condense on the substrate to generate the co-crystal(s).

Process parameters for the OVCC may be controlled to influence the resulting deposit morphology of the co-crystals. These process parameters may include, but are not limited to, evaporation source temperature, substrate temperature, inlet flow rates, nozzle-substrate separation, raster velocity, dilution flow rate ($Q_{DIL}$), guard flow gas flow rate ($Q_{GF}$), and working pressure.

If the organic compound and coformer have similar sublimation characteristics (e.g. vapor pressure) a common evaporation temperature may be used, with an apparatus configuration shown here that incorporates the common heating shroud 311. In other exampels, a configuration provides for individually controlling the temperature of each organic compound source, i.e., for each tube 320 and 330, in which case separate heating elements may be used, one for each tube 320 and 330. FIG. 1 shows the co-crystal formation system 300 used to form a co-crystal. The heating shroud 311 controlled the vapor mixing chamber temperature ($T_{source}$). Each of the two inner chambers 320 and 330, which act as thinner evaporation nozzles with their own inlets (325-1, 335-1), are inserted into the larger vapor mixing chamber 307 from the top. Each of these chambers 320 and 330, receive their own flow of carrier gases, allowing the individual organic compounds to be jetted into the larger mixing chamber 307. The organic compounds were contained in source boats located within the thinner evaporation nozzles 320-1 and 330-1. The mixing gas flow inlet 308 was used, as well. During the process, the organic vapor combination was jetted onto the chilled substrate 360, which is externally cooled to maintain a constant temperature ($T_{sub}$). The guard flow inlet 309 was not used in this particular example. It is noted, that the lower region 350 and the inlet 309 region could be used to incorporate a tertiary component in to the system 300. For pharmaceutical solids, for example, a tracer compound may be often added to drug products to prevent tampering and imitation products. For example, an organic dye can be added to give the product a specific color. Similarly, a tertiary compound can be entered into the OVCC process of system 300. For example, a small quantity of organic dye could be deposited in addition to other organic compounds, thereby changing the color of the film without changing the structure of the co-crystal.

Figure 2:
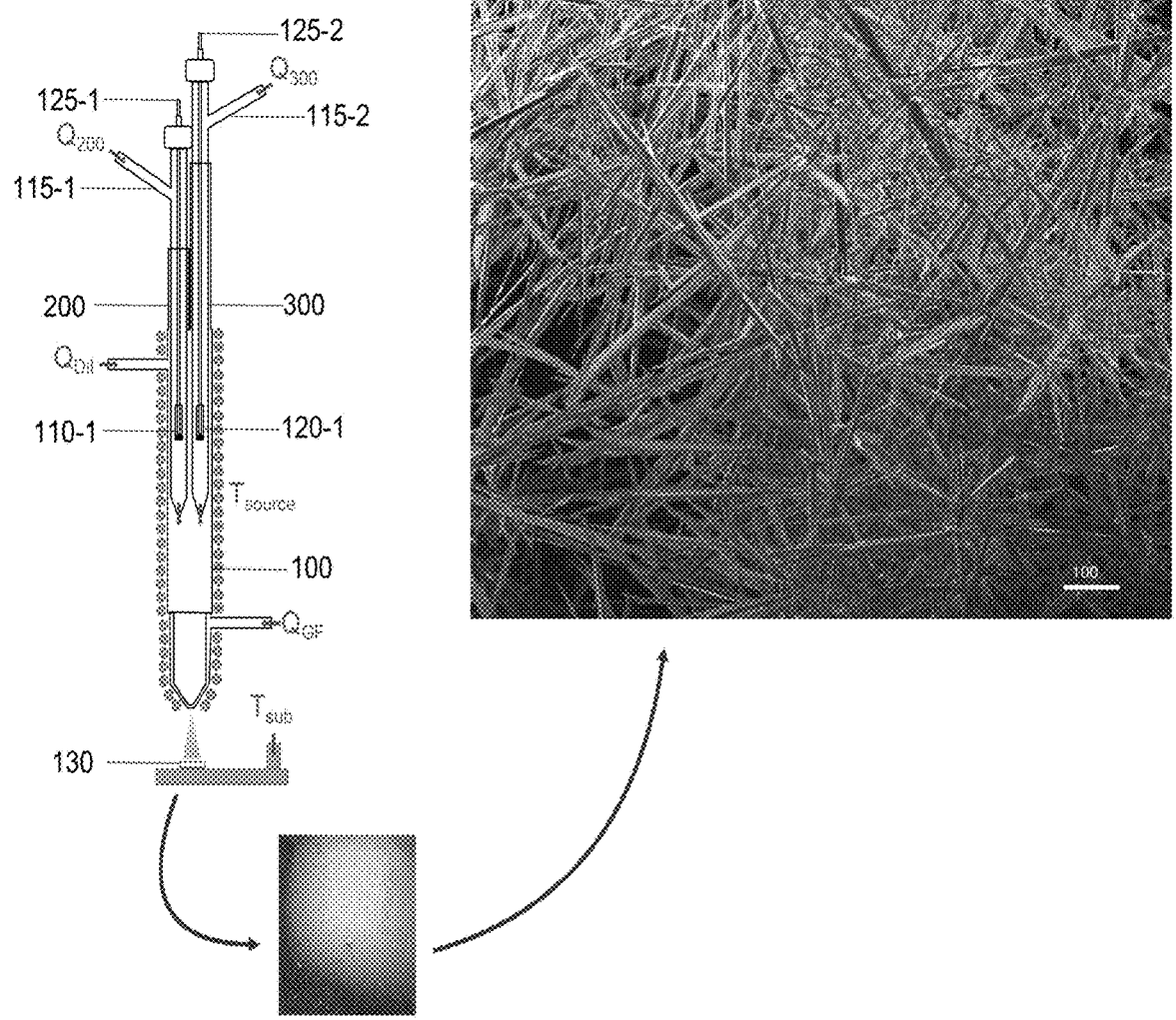
FIG. 2 depicts an embodiment of a dual nozzle OVCC apparatus disclosed herein with an example of a co-crystal film deposited on a 1 mm glass substrate using the method and apparatus described herein, as well as a scanning electron microscope ("SEM") image of the crystal morphology of the co-crystal film produced by the method and apparatus described herein.

FIG. 2 illustrates a co-crystal formation system that was used to prepare caffeine-succinic acid co-crystals.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

The following examples are provided for illustration and are not intended to limit the scope of the invention.

Characterization Methods

X-ray diffraction ("XRD") data were obtained by scanning samples in continuous mode from 4-60° (2θ) with a step size of 0.02° at 40 kV and 40 mA with CuKα radiation (1.54 Å).

Differential scanning calorimetry ("DSC") was performed on a calorimeter in an aluminum crimped pan, TA Q20 DSC in a Tzero Low-Mass Pan under dry nitrogen.

Scanning electron microscopy ("SEM") was performed using a JSM-IT500 InTouchScope™ Scanning Electron Microscope. All samples were imaged as is without any gold sputtering or surface treatment prior to use. The instrument was operated in high vacuum mode with an accelerating voltage of 3 kV. Images were taken at various magnifications within the range of 100× to 4000×, and were later post processed to improve contrast and brightness.

Thermogravimetric analysis ("TGA") was performed on a TA Instruments Q500 TGA. All samples were in characterized in powdered form, without any prior purification or milling steps. Each run was carried out using approximately 5 to 10 mg of powdered organic material, which was placed into a tared platinum pan. The mass of the organic was measured as the temperature was ramped up at a rate of 5° C./min, from 25 to 500° C.

Example 1: Synthesis of Caffeine/Succinic Acid Co-Crystals

While initial experiments to generate caffeine-succinic acid co-crystals attempted to co-deposit the two materials in 1:1 or similar ratios, they had not succeeded. These initial experiments were carried out at a source temperature of 140° C., which corresponds to the onset of sublimation as determined by thermogravimetric analysis (TGA). Increasing the source temperature significantly above (e.g. by 30° C.) this temperature achieved a greater concentration of organic compound in the vapor phase. The partial pressure of the inert gas used in the process also had to be limited to decrease the molar fraction of carrier gas while increasing the molar fraction of the organic vapor. At the same time, it was also found that some nitrogen flow was required to achieve adequate local deposition rate. Both can be achieved by minimizing the dilution flow rate (e.g. below 30 sccm) in the larger mixing nozzle. Generally, the higher the level of saturation of organic compound in the vapor phase, the greater will be the overall driving force for co-crystal formation.

All substrates used were cleaned and prepared in the same way. Substrates were first cut into approximately 1 cm×1 cm squares using a diamond scoring tool. They were then sonicated in a solution of DI water+Tergitol at 40° C. for 10 minutes. The substrates were then rinsed with fresh DI water to remove any residual soap suds, and again sonicated in fresh DI water at 40° C. for 10 minutes. The substrates were then rinsed with acetone, and sonicated in fresh acetone at 40° C. for 10 minutes. The substrates were then rinsed with isopropanol (IPA) to remove any residual acetone, and sonicated in fresh IPA at 40° C. for 10 minutes. Finally, the substrates were once again rinsed with fresh IPA, and boiled in IPA at 215° C. for 5 minutes. Following this, the substrates were dried with a nitrogen (N2) gun and stored in a sealed container.

During the deposition step, the source temperature was kept constant by a PID temperature controlled and thermocouple insert in each nozzle. When necessary, the substrate temperature was maintained using PID process control, e.g. in this case using a closed-loop recirculation system. The three inlet flow rates were kept constant using three separate mass flow controllers. This is different from traditional OVJP in which only a single mass flow controller is used. The entire nozzle was rastered over the substrate using an XY stage with motor controls. The nozzle separation was controlled and kept constant using a Z motor control. Alternatively, the substrate was kept still in one or more axes while the nozzle was moved using XYZ controls over the nozzle alone. Following the deposition step, the samples were kept sealed in the same container until they could be characterized using x-ray diffraction (XRD), scanning electron microscopy (SEM), and/or differential scanning calorimetry (DSC).

Stable co-crystals of caffeine and succinic acid were synthesized using the apparatus depicted in FIG. 2. The codeposited organic film is the white square region in the bottom left of the glass substrate. Because the nozzle was kept some distance from the substrate (4 mm), there is some spreading of organic compound around the film. The film was rastered over the substrate keeping the center to center line spacing (0.2 mm) and raster velocity (0.25 mm/s) constant. The SEM image was taken at 100× magnification. The crystal exhibits a unique needle like morphology, which shows no preferred orientation attributed to the fact that the nozzle was rastered rather than dwelled over a single spot. The long needles are approximately 10 to 20 microns wide and anywhere from 50 to 100 microns in length.

Figure 3:
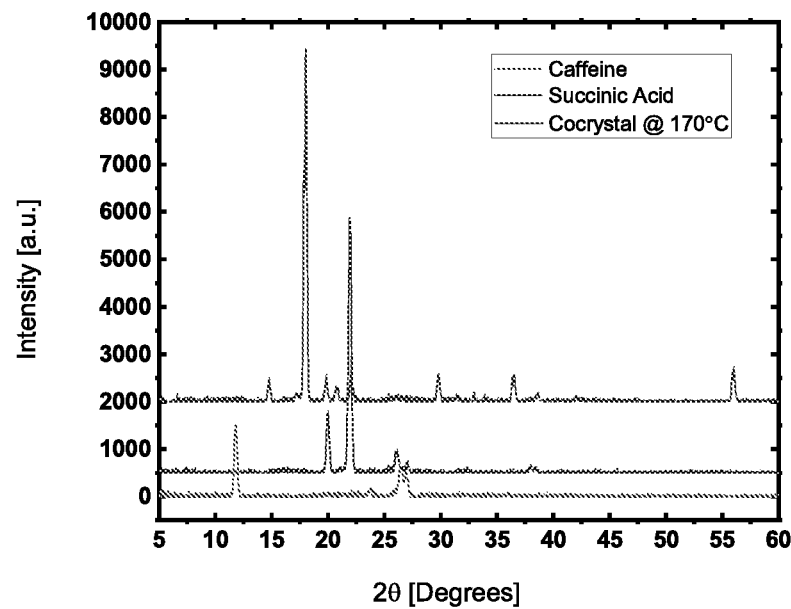
FIG. 3 depicts an X-ray diffraction pattern of pure caffeine (organic compound, bottom trace), pure succinic acid (co-former, middle trace), and a co-crystal of caffeine and succinic acid (top trace).

The XRD plot in FIG. 3 shows the theta/2theta scan for a pure caffeine film (bottom) and a pure succinic acid film (middle). Above this, the scan for the co-crystal sample is shown (top). The co-crystal sample shows new peaks around 14°, 18°, and 22°, which is indicative of a new crystalline phase. The main peak for caffeine around 11° is not present, indicating that the pure drug has all reacted to form the co-crystalline phase. Some residual peaks corresponding to succinic acid are still present, indicating that there is some excess pure succinic acid remaining.

The DSC scan in FIG. 4 shows the results of testing pure caffeine powder, pure succinic acid powder, and the codeposited drug film of caffeine and succinic acid co-crystals, which was scraped off the substrate. The co-crystal film tested is the same one showed in the SEM image and the XRD plot. Caffeine shows an endotherm around 237° C., corresponding to its known melting point. Succinic acid shows an endotherm around 188° C., corresponding to its known melting point. The co-crystal film shows a new endotherm around 116° C., which is indicative of a new phase with a lower melting point. There is some residual endothermic behavior at higher temperatures, which is attributed to the excess succinic acid coformer remaining in the sample. The lower melting temperature of the co-crystal, which generally corresponds to a higher solubility.

FIG. 5 shows morphological comparison between deposited films of caffeine, succinic acid, and its co-crystal. All three films were deposited under the same conditions in regard to source temperature, substrate temperature, nozzle flow rates, separation distance, and raster conditions. The SEM images shown were all taken at the same magnification (1000×) to show a clear comparison at a set size range. The caffeine film shows the previously described hollow pillar morphology, with uniform particles on the order of 50 microns. The succinic acid film shows the previously described fractal morphology composed of plates with a broader particle size distribution in the range of 50 to 100 microns. The co-crystal film differs from the previously described morphology as it was deposited at a source temperature that was 5° C. lower. Because of this, less material was deposited and thus the crystals did not grow as much to the lengths. One still sees the beginnings of the needle like morphology, which branch out from aggregates that are on the order of 25 to 50 microns. The chemical structure of each system is shown below its respective micrograph.

Example 2: Example of Co-Crystal Indomethacin/Saccharine

Thermogravimetry analysis (TGA) of both the organic compound indomethacin and the coformer saccharine is performed on a TA Instruments TGA 550 over a 25-300° C. range at a heating rate of 5° C. per minute to initially characterize the components' sublimation properties, followed by collecting several isotherms (Shalev O, Shtein M., Org. Electron., 2013, 14, 94). Isothermal evaporation rates are also measured, where the pure materials are first heated to a starting temperature of 120° C., after which the temperature is held constant for 10 minutes, then raised in ten-degree increments and held for 10 minutes at each set point, up to and including 170° C. For all experiments, the sample purge is set at 40 mL/min and the balance purge is set at 20 mL/min flow of nitrogen (purity≥99.9%).

The cocrystal deposition apparatus consists of a heated glass tube approximately 2.5 cm in diameter, with a conical outlet, containing two similar, smaller diameter source tubes. Inside the source tubes indomethacin and the coformer saccharine are individually loaded and positioned along the temperature gradient to achieve a desired evaporation temperature for each material, regulated by an external Cole Par-mer Digi-Sense Temperature Controller. The carrier gas is nitrogen (purity≥99.9%), metered into each inlet via Sierra Instruments Smart-Trak 2 Digital Mass Flow Controllers. For simplicity, the positions of organic compound and coformer are kept identical throughout the experiment, such that an increase in temperature produced a progressive increase in the ratio of the more volatile to the less volatile material in the gas stream. The nozzle is rastered across the substrate in a snake-like path to coat an area.

The source temperature is modified in a manner such that the vapor pressure increases exponentially with temperature. The partial pressure of the inert gas used in the process also is limited to decrease the molar fraction of carrier gas while increasing the molar fraction of the organic vapor. The dilution flow rate (e.g. below 30 sccm) is minimized in the larger mixing nozzle. Generally, the higher the level of saturation of organic compound in the vapor phase, the greater will be the overall driving force for co-crystal formation.

All substrates are cleaned and prepared in the same way. The substrates are first cut into approximately 1 cm×1 cm squares using a diamond scoring tool. They are then sonicated in a solution of DI water+Tergitol at 40° C. for 10 minutes. After sonication, the substrates are rinsed with fresh DI water to remove any residual soap suds, and again sonicated in fresh DI water at 40° C. for 10 minutes. The substrates are then rinsed with acetone, and sonicated in fresh acetone at 40° C. for 10 minutes. After sonication in fresh acetone, the substrates are rinsed with isopropanol (IPA) to remove any residual acetone, and sonicated in fresh IPA at 40° C. for 10 minutes. Finally, the substrates are once again rinsed with fresh IPA, and boiled in IPA at 215° C. for 5 minutes. Following this, the substrates are dried with a nitrogen (N2) gun and stored in a sealed container.

During the deposition step, the source temperature is kept constant by a PID temperature controlled and thermocouple insert in each nozzle. When necessary, the substrate temperature is maintained using PID process control, e.g. in this case using a closed-loop recirculation system. The three inlet flow rates are kept constant using three separate mass flow controllers. This is different from traditional OVJP in which only a single mass flow controller is used. The entire nozzle is rastered over the substrate using an XY stage with motor controls. The nozzle separation is controlled and kept constant using a Z motor control. Alternatively, the substrate can be kept still in one or more axes while the nozzle is moved using XYZ controls over the nozzle alone. Following the deposition step, the samples are kept sealed in the same container until they can be characterized using x-ray diffraction (XRD), scanning electron microscopy (SEM), and differential scanning calorimetry (DSC).

Stable co-crystals of indomethacin and the coformer saccharine are synthesized using the apparatus depicted in FIG. 1.

Example 3: Depositing Co-Crystals to Substrates

Metal Substrate

A metal substrate, such as a medical needle, is cleaned and prepared prior to depositing the co-crystals. The metal substrate is sonicated in a solution of DI water+Tergitol at 40° C. for 10 minutes. The metal substrate is then rinsed with fresh DI water to remove any residual soap suds, and again sonicated in fresh DI water at 40° C. for 10 minutes. After sonication in fresh DI water, the metal substrate is rinsed with acetone, and sonicated in fresh acetone at 40° C. for 10 minutes. The metal substrate is then rinsed with isopropanol (IPA) to remove any residual acetone, and sonicated in fresh IPA at 40° C. for 10 minutes. Finally, the metal substrate is once again rinsed with fresh IPA, and boiled in IPA at 215° C. for 5 minutes. Following this, the metal substrate is dried with a nitrogen (N2) gun and stored in a sealed container.

During the deposition step, the source temperature is kept constant by a PID temperature controlled and thermocouple insert in each nozzle. When necessary, the substrate temperature is maintained using PID process control, e.g. in this case using a closed-loop recirculation system. The three inlet flow rates are kept constant using three separate mass flow controllers. This is different from traditional OVJP in which only a single mass flow controller is used. The entire nozzle is rastered over the substrate using an XY stage with motor controls. The nozzle separation is controlled and kept constant using a Z motor control. Alternatively, the substrate can be kept still in one or more axes while the nozzle is moved using XYZ controls over the nozzle alone. Following the deposition step, the samples are kept sealed in the same container until they can be characterized using x-ray diffraction (XRD), scanning electron microscopy (SEM), and differential scanning calorimetry (DSC).

Polymer Substrate

A polymer substrate, such as a plastic hypodermic needle, is cleaned and prepared prior to depositing the co-crystals. The polymer substrate can be cleaned by autoclaving, exposing to UV light, UV-ozone atmosphere or oxygen plasma, or being treated with alcohol wipes, or sonicated in soapy water. During the deposition step, the source temperature is kept constant by a PID temperature controlled and thermocouple insert in each nozzle. When necessary, the substrate temperature is maintained using PID process control, e.g. in this case using a closed-loop recirculation system. The three inlet flow rates are kept constant using three separate mass flow controllers. This is different from traditional OVJP in which only a single mass flow controller is used. The entire nozzle is rastered over the substrate using an XY stage with motor controls. The nozzle separation is controlled and kept constant using a Z motor control. Alternatively, the substrate can be kept still in one or more axes while the nozzle is moved using XYZ controls over the nozzle alone. Following the deposition step, the samples are kept sealed in the same container until they can be characterized using x-ray diffraction (XRD), scanning electron microscopy (SEM), and differential scanning calorimetry (DSC).

Fabric Substrate

A fabric substrate, such as a medical bandage, is cleaned and prepared prior to depositing the co-crystals. The fabric substrate can be cleaned by autoclaving, exposing to UV light, UV-ozone atmosphere or oxygen plasma, or being treated with alcohol wipes, or sonicated in soapy water. During the deposition step, the source temperature is kept constant by a PID temperature controlled and thermocouple insert in each nozzle. When necessary, the substrate temperature is maintained using PID process control, e.g. in this case using a closed-loop recirculation system. The three inlet flow rates are kept constant using three separate mass flow controllers. This is different from traditional OVJP in which only a single mass flow controller is used. The entire nozzle is rastered over the substrate using an XY stage with motor controls. The nozzle separation is controlled and kept constant using a Z motor control. Alternatively, the substrate can be kept still in one or more axes while the nozzle is moved using XYZ controls over the nozzle alone. Following the deposition step, the samples are kept sealed in the same container until they can be characterized using x-ray diffraction (XRD), scanning electron microscopy (SEM), and differential scanning calorimetry (DSC).

Intraocular Lens

An intraocular lens was cleaned and prepared prior to depositing the co-crystals (such as a caffeine and succinic acid co-crystal shown in FIG. 14). The intraocular lens can be cleaned by autoclaving, exposing to UV light, UV-ozone atmosphere or oxygen plasma, or being treated with alcohol wipes, or sonicated in soapy water. During the deposition step, the source temperature was kept constant by a PID temperature controlled and thermocouple insert in each nozzle. When necessary, the substrate temperature was maintained using PID process control, e.g. in this case using a closed-loop recirculation system. The three inlet flow rates were kept constant using three separate mass flow controllers. This is different from traditional OVJP in which only a single mass flow controller is used. The entire nozzle was rastered over the substrate using an XY stage with motor controls. The nozzle separation was controlled and kept constant using a Z motor control. Alternatively, the substrate was kept still in one or more axes while the nozzle was moved using XYZ controls over the nozzle alone. Following the deposition step, the samples were kept sealed in the same container until they could be characterized using x-ray diffraction (XRD), scanning electron microscopy (SEM), and/or differential scanning calorimetry (DSC).

As shown in FIG. 14, the intraocular lens was coated with caffeine and succinic acid co-crystals on the "wings" of the lens, so as not to obstruct the vision of a potential patient.

Example 4: Process Flow—Generating a Co-Crystal Composition

Figure 10:
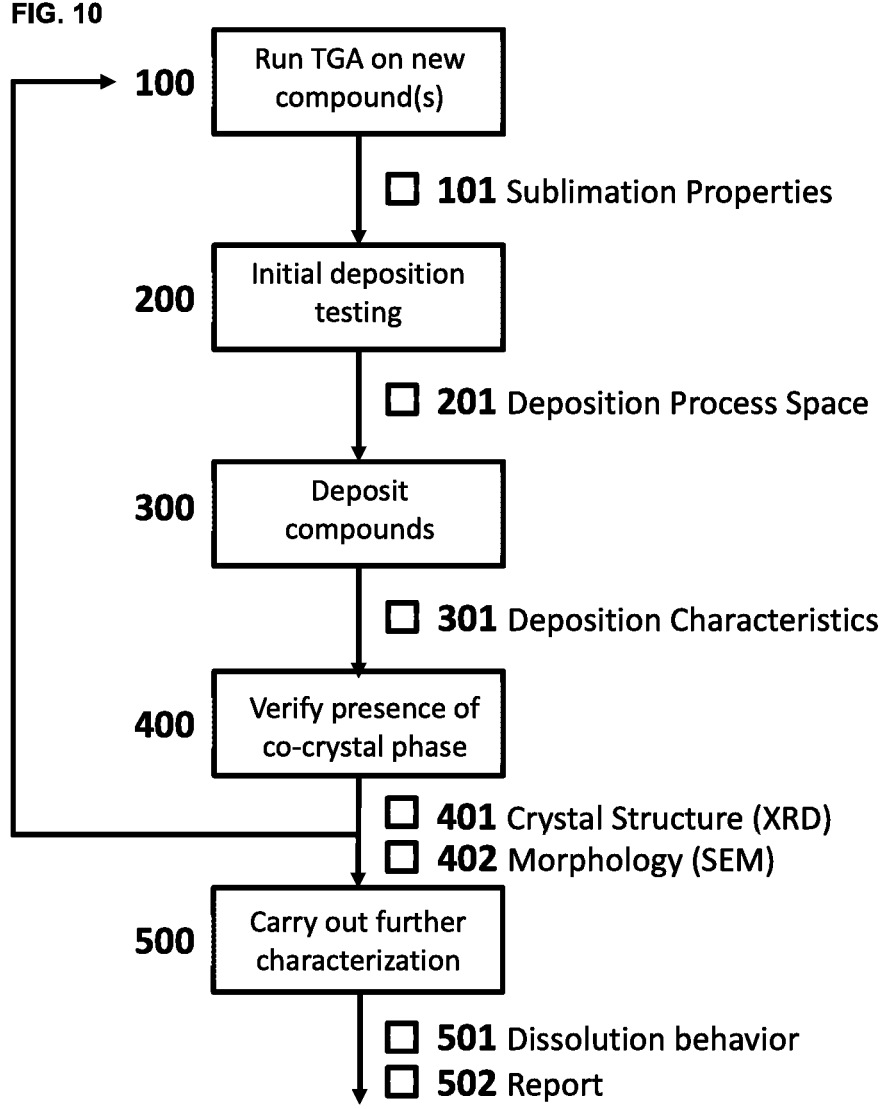
FIG. 10 depicts an example of a process flow for discovering or generating a co-crystal using the methods described herein.

FIG. 10 shows the process flow for discovering or generating a co-crystal utilizing a method described herein. After obtaining a new organic compound of interest, such as an API, the first step is to run thermogravimetric analysis (TGA) to determine key sublimation properties. These include enthalpy of vaporization ($\Delta H_{vap}$), enthalpy as a function of temperature, and vapor pressure as a function of temperature, all of which can be used to calculate deposition rate for a set of process parameters. Once the deposition rate is calculated, the next step is to perform initial deposition testing with a variety of available coformers to prescreen for possible combinations. This can be done in conjunction with literature search for known co-crystal combinations, as well as computational screening using the Cambridge Structural Database (CSD). Upon determination of an ideal API-coformer system, as well as the deposition rates required, the compounds are deposited using the OVCC apparatus to form a film on a specified substrate. Characterization through XRD and SEM must be carried out to probe for changes in crystal structure and morphology as compared to deposited films of the pure compounds. This is done to verify that a co-crystal has been formed and the two compounds have not merely been codeposited. If the latter is the case, one must go back to step one and determine what changes need to be made in terms of compound selection or processing parameters to create a co-crystal with the given API. If a co-crystal phase is present in the sample, further characterization can be carried out through dissolution testing to determine the impact of the co-crystalization on the dissolution properties of the API in solution. Finally, the data can be reported and used to further future understanding of the way in which co-crystals form and improve the dissolution characteristics of poorly soluble drugs.

Example 5: Process Flow—Obtain Co-Crystal Design

Figure 11:
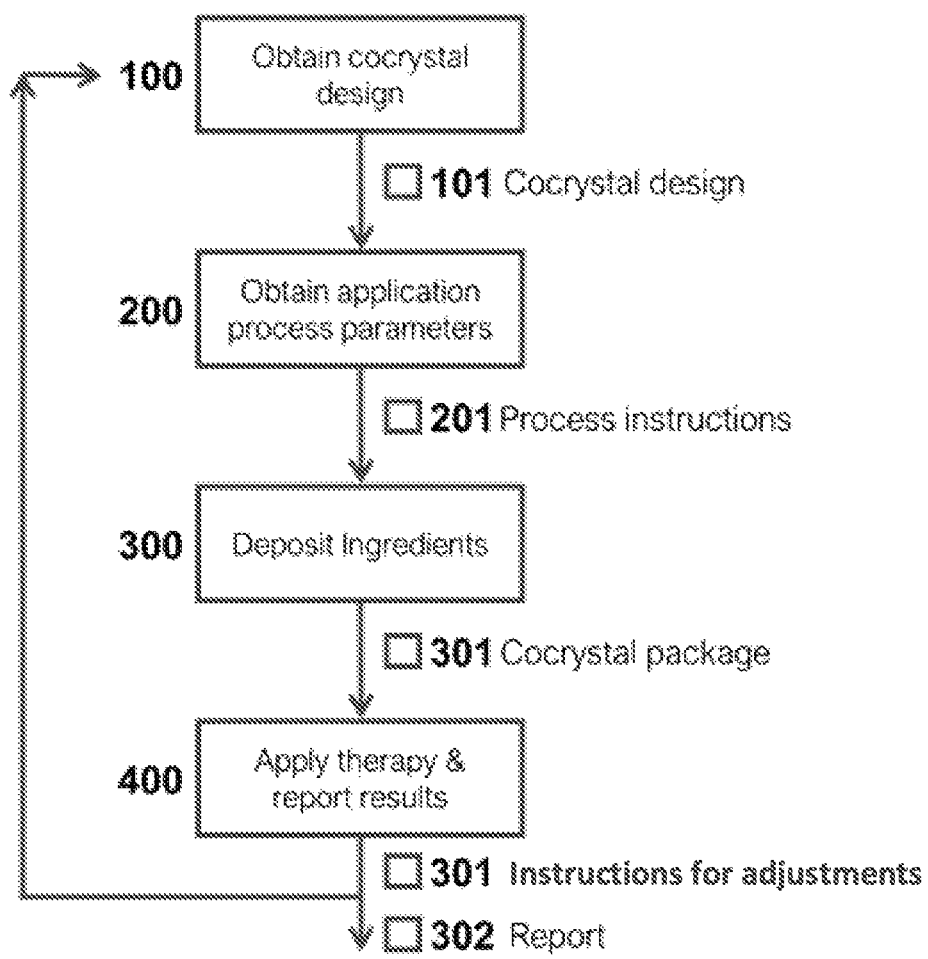
FIG. 11 depicts an example of the overall process flow and logic behind the synthesis of a co-crystal using the methods and apparatuses described herein, once a co-crystal design is obtained.

FIG. 11 shows the process flow for obtaining a co-crystal design. Initial steps involve obtaining the appropriate co-crystal design, for commercial or research purposes. Following this, application and process parameters would need to be determined for the system. This includes pre-deposition characterization of the precursor compounds and calibration of the apparatus with said compounds regarding heating and flow rate. Once the system is calibrated, the compounds are deposited to form the co-crystal film and collected appropriately. Following deposition, the co-crystals are applied to the therapy desired and the results are reported. This step also acts as a feedback loop to instruct operators on and adjustments that need to me made to prior steps in the process.

Figure 12:
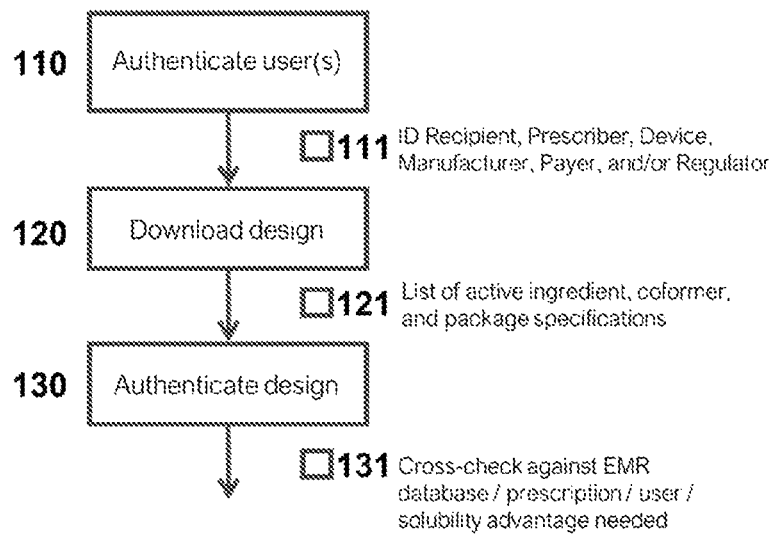
FIG. 12 depicts an expanded view of section 100 in FIG. 11.

FIG. 12 expands upon section 100 of FIG. 11. In obtaining the co-crystal design, one must go through a series of steps. First, the user must be authenticated, whether it be an ID recipient, prescriber, device manufacturer, payer, or regulator. This will help dictate following steps to ensure the product meets specifications. The design must then be obtained as a list of active ingredients, coformer, and package specifications. Finally, the design must be authenticated via cross-check against the EMR database, along with verifying the prescription, user, and solubility advantage needed.

Figure 13:
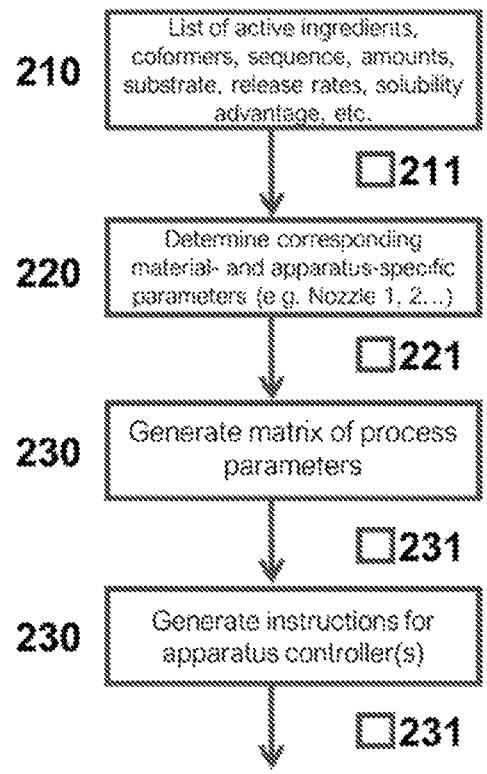
FIG. 13 depicts an expanded view of section 200 in FIG. 11.

FIG. 13 expands upon section 200 of FIG. 11. In obtaining the application and process parameters, one must go through a series of steps. First, the list of active ingredients, coformers, sequence, amounts, substrates, release rates, solubility advantage desired, etc. must be determined. Next, the corresponding material- and apparatus-specific parameters (e.g. Nozzle 1, 2 . . . ) must be determined. Following this, one must generate a matrix of process parameters. Finally, one generates the instructions for the apparatus controller and move into section 300 of FIG. 11.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

We claim:

1. A method of forming a co-crystal of an organic compound and a coformer comprising:
   (a) subliming and/or evaporating the organic compound optionally in the presence of an organic compound carrier gas to form an organic compound vapor;
   (b) subliming and/or evaporating the coformer optionally in the presence of a coformer carrier gas to form a coformer vapor;
   (c) mixing the organic compound vapor and the coformer vapor, optionally in the presence of a mixing gas, to form a vapor mixture, wherein the vapor mixture comprises a molar ratio of the organic compound and the coformer of 10:1 to 1:10; and
   (d) condensing the vapor mixture onto a substrate to form the co-crystal;
   wherein:
   the co-crystal comprises the organic compound and the coformer hydrogen bonded together, optionally in a ratio of 1:3 to 3:1;
   the organic compound is sublimed at a temperature that is 10° C. to 100° C. above its onset of sublimation, as determined by thermogravimetric analysis ("TGA");
   the substrate is at a temperature of −50° C. to 50° C.;
   and the co-crystal is stable at 25° C., characterized by differential scanning calorimetry, microscopy, X-ray diffraction, or a combination thereof.

2. The method of claim 1, wherein the substrate is coated with the co-crystal during step (d).

3. The method of claim 1, wherein the organic compound has a vapor pressure of $10^{-3}$ Pascals to $10^{6}$ Pascals.

4. The method of claim 1, wherein the organic compound is an active pharmaceutical ingredient, optionally wherein the organic compound is selected from the group consisting of caffeine, carbamazepine, 5-methoxy sulfadiazine, ethenzamide, nalidixic acid, isoniazid, furosemide, sulfadimidine, celecoxib, temozolamide, piroxicam, tryptamine, chlorzoxazone, p-coumaric, itraconazole, fluoxetine, telaprevir, sildenafil, theophylline, aceclofenac, 5-nitrouracil, indomethacin, aripiprazole, and atorvastatin, or a mixture thereof.

5. The method of claim 1, wherein the coformer comprises one or more hydrogen bonding functional groups, optionally wherein the coformer comprises a carboxylic acid, alcohol, ketone, aldehyde, amide, amine, heterocycle comprising at least one N or O ring atom, or combinations thereof.

6. The method of claim 1, wherein the coformer is selected from the group consisting of benzoic acid, oxalic acid, malonic acid, succinic acid, maleic acid, fumaric acid, glutaric acid, adipic acid, pimelic acid, 3,5-dihydroxybenzoic acid, trifluoroacetic acid, 2,5-dihydroxybenzoic acid, 2,4-dihydroxybenzoic acid, m-nitrobenzoic acid, 5-chlorosalicylic acid, saccharin, citric acid, tartaric acid, 2,3-dihydroxybenzoic acid, 3,4-dihydroxybenzoic acid, barbital, 4-hydroxybenzoic acid, 1-hydroxy-2-naphthoic acid, malic acid, 3-hydroxybenzoic acid, 6-hydroxy-2-naphthoic acid, methylgallate, salicylic acid, 2-hydroxybenzoic acid, formic acid, 3-hydroxy-2-naphthoic acid, sulfacetamide, acetic acid, sulfaproxyline, sulfuric acid, sulfamic acid, ethylenediamine, octadecylamine, glucono-delta lactone, allocitric acid, sucralose, indole, 1-hydroxyethyldene-1,1-diphosphonic acid, skatole, 5-chlorosalicylic acid, urea, 5-nitroisophthalic acid, trimesic acid, gentisic acid, ketoglutaric acid, adamantine tricarboyxlic acid, t-butylhydroquinone, isocitric acid, trifluoroethanol, camphoric acid, 4-aminobenzoic acid, 2,6-pyridinedicarboxylic acid, aspirin, butyric acid, formamide, nicotinamide, nitromethane, 1,4-benzoquinone, glycolic acid, terephthalaldehyde, dioxane, N-methylpyrrolidone, dimethylsulfoxide, dimethylacetamide, acetone, dimethylformamide, furfural, and 4,4'-bipyridine, or a mixture thereof.

7. The method of claim 1, wherein step (a) is performed in the presence of the organic compound carrier gas, and/or step (b) is performed in the presence of the coformer carrier gas, and/or step (c) is performed in the presence of the mixing gas.

8. The method of claim 7, wherein the organic compound carrier gas carries the organic compound to a mixing chamber prior to step (c), and/or the coformer carrier gas carries the coformer to a mixing chamber prior to step (c), and/or the mixing gas carries the vapor mixture to the substrate.

9. The method of claim 7, wherein the organic compound carrier gas, and/or the coformer carrier gas, and/or the mixing gas has a flow rate of about 1 to 150 standard cubic centimeters per minute ("sccm").

10. The method of claim 1, further comprising exposing the mixing gas to a guard flow gas prior to step (d), such that the guard flow gas surrounds the mixing gas, and the mixing gas comprises the vapor mixture.

11. The method of claim 1, wherein the substrate has a temperature of 5° C. to 25° C.

12. The method of claim 1, wherein the substrate is a medical device, optionally wherein the medical device is selected from the group consisting of a stent, needle, microneedle, probe, syringe, cannula, catheter, sponge, clip, mesh, bandage, gauze, dressing, tape, swab, burn dressing, staple, implant, contact lens, medical tubing, adhesive patches, artificial tissue, intraocular lens, endoscopic device, punctal plugs, buccal patches, lingual patches, sub-lingual patches, electrode patches, and combinations thereof.

13. The method of claim 1 further comprising moving the vapor mixture over the substrate during step (d).

14. The method of claim 1 further comprising moving the substrate under the vapor mixture during step (d).

15. A substrate coated with a co-crystal produced by the method of claim 1.

16. A co-crystal produced by the method of claim 1.

17. The co-crystal of claim 16, wherein the co-crystal comprises caffeine and succinic acid or indomethacin and saccharine.

18. A co-crystal comprising caffeine and succinic acid, characterized by an X-ray diffraction ("XRD") pattern comprising peaks at 14, 18, and 22±0.2° 2θ using Cu Kα radiation.

19. A pharmaceutical composition comprising the co-crystal of claim 16 and a pharmaceutically acceptable carrier.

20. An apparatus for producing a co-crystal comprising a housing having
  (i) a vapor mixing chamber adjacent to a jet exiting nozzle end of the housing; and
  (ii) a receiving end opposite the jet exiting nozzle end;
the vapor mixing chamber being adjacent to a temperature control shroud for controlling the temperature of a vapor mixture of the organic compound and the coformer in the vapor mixing chamber;
a first tubular internal container for injecting an organic compound and positioned within the receiving end, having
  (i) an outlet nozzle for feeding the organic compound into the vapor mixing chamber;
  (ii) an organic compound carrier gas inlet tube; and
  (iii) a thermocouple at a proximal end for controlling evaporation temperature of the first tubular internal container; and
a second tubular internal container for injecting the coformer and positioned within the receiving end, having
  (i) an outlet nozzle for feeding the coformer into the vapor mixing chamber,
  (ii) a coformer carrier gas inlet tube, and
  (iii) a thermocouple at a proximal end for controlling evaporation temperature of the second tubular internal container,
wherein at least one of the first tubular container and the second tubular container has a mixing gas inlet.

* * * * *